(12) United States Patent
Crystal et al.

(10) Patent No.: US 12,122,844 B2
(45) Date of Patent: *Oct. 22, 2024

(54) TREATMENT OF BRAIN CANCERS USING CENTRAL NERVOUS SYSTEM MEDIATED GENE TRANSFER OF MONOCLONAL ANTIBODIES

(71) Applicants: Cornell University, Ithaca, NY (US); Memorial Sloan-Kettering Cancer Center, New York, NY (US)

(72) Inventors: Ronald G. Crystal, New York, NY (US); Stephen M. Kaminsky, Bronx, NY (US); Martin J. Hicks, New York, NY (US); Viviane Tabar, New York, NY (US)

(73) Assignees: Cornell University, Ithaca, NY (US); Memorial Sloan-Kettering Cancer Center, New York, NY (US)

( * ) Notice: Subject to any disclaimer, the term of this patent is extended or adjusted under 35 U.S.C. 154(b) by 494 days.

This patent is subject to a terminal disclaimer.

(21) Appl. No.: 16/927,675

(22) Filed: Jul. 13, 2020

(65) Prior Publication Data
US 2021/0171656 A1 Jun. 10, 2021

Related U.S. Application Data

(63) Continuation of application No. 14/426,347, filed as application No. PCT/US2013/059674 on Sep. 13, 2013.

(60) Provisional application No. 61/700,599, filed on Sep. 13, 2012.

(51) Int. Cl.
| | |
|---|---|
| *C07K 16/30* | (2006.01) |
| *A61K 39/00* | (2006.01) |
| *A61K 48/00* | (2006.01) |
| *C07K 16/22* | (2006.01) |
| *C07K 16/24* | (2006.01) |
| *C07K 16/28* | (2006.01) |

(52) U.S. Cl.
CPC ........ *C07K 16/3053* (2013.01); *A61K 48/005* (2013.01); *C07K 16/22* (2013.01); *C07K 16/24* (2013.01); *C07K 16/2863* (2013.01); *A61K 2039/505* (2013.01); *A61K 48/00* (2013.01); *C07K 2317/21* (2013.01); *C07K 2317/24* (2013.01); *C12N 2750/14141* (2013.01); *C12N 2799/025* (2013.01)

(58) Field of Classification Search
CPC ............ C07K 16/3053; C07K 16/2863; A61K 48/00–0091
See application file for complete search history.

(56) References Cited

U.S. PATENT DOCUMENTS

| | | | |
|---|---|---|---|
| 5,212,290 A | 5/1993 | Vogelstein et al. | |
| 6,884,879 B1 | 4/2005 | Baca et al. | |
| 7,691,977 B2 | 4/2010 | Fuh et al. | |
| 7,723,484 B2 | 5/2010 | Beidler et al. | |
| 8,012,936 B2 | 9/2011 | Sigurdsson et al. | |
| 8,592,149 B2 | 11/2013 | Ramakrishnan | |
| 8,703,137 B2 | 4/2014 | Chain | |
| 8,745,386 B2 | 6/2014 | Ureche et al. | |
| 8,748,386 B2 | 6/2014 | Sigurdsson | |
| 9,840,560 B2 | 12/2017 | Alper | |
| 10,946,094 B2* | 3/2021 | Crystal | A61K 31/4745 |
| 12,024,568 B2 | 7/2024 | Crystal et al. | |
| 2003/0211097 A1 | 11/2003 | Pastan et al. | |
| 2006/0034805 A1 | 2/2006 | Fang et al. | |
| 2006/0051322 A1 | 3/2006 | Tuszynski | |
| 2009/0269336 A1 | 10/2009 | Hong et al. | |
| 2010/0291549 A1 | 11/2010 | Ramakrishnan | |
| 2010/0316564 A1 | 12/2010 | Sigurdsson | |
| 2011/0171210 A1 | 7/2011 | Marasco et al. | |
| 2011/0318358 A1 | 12/2011 | Sigurdsson et al. | |
| 2012/0207671 A1 | 8/2012 | Baldwin | |
| 2012/0244174 A1 | 9/2012 | Chain | |
| 2013/0090375 A1* | 4/2013 | Crystal | A61P 27/02 514/44 R |
| 2013/0158104 A1 | 6/2013 | Tubert et al. | |
| 2013/0195801 A1 | 8/2013 | Gao et al. | |
| 2014/0302046 A1 | 10/2014 | Sigurdsson | |
| 2014/0336245 A1 | 11/2014 | Mingozzi et al. | |
| 2015/0210771 A1 | 7/2015 | Crystal et al. | |
| 2016/0024193 A1 | 1/2016 | Ayalon et al. | |
| 2016/0355573 A1 | 12/2016 | Crystal et al. | |
| 2020/0172605 A1 | 6/2020 | Crystal et al. | |

FOREIGN PATENT DOCUMENTS

| | | |
|---|---|---|
| CN | 103772501 A | 5/2014 |
| JP | 2007-526756 A | 9/2007 |
| WO | WO-0054057 A1 | 9/2000 |
| WO | WO-2011133890 A1 | 10/2011 |
| WO | WO-2012045882 A2 | 4/2012 |
| WO | WO-2013151763 A1 | 10/2013 |

(Continued)

OTHER PUBLICATIONS

Muller et al. Structure 6(9): 1153-1167 (Year: 1998).*

(Continued)

*Primary Examiner* — Jessica H Roark
(74) *Attorney, Agent, or Firm* — Schwegman Lundberg & Woessner, P.A.

(57) ABSTRACT

The invention provides methods to inhibit or treat brain cancers by locally inhibiting expression or activity of growth factors or growth factor receptors.

14 Claims, 8 Drawing Sheets

Specification includes a Sequence Listing.

(56) References Cited

FOREIGN PATENT DOCUMENTS

| WO | WO-2014043480 A1 | 3/2014 |
|---|---|---|
| WO | 2014100600 | 6/2014 |
| WO | WO-2014152157 A2 | 9/2014 |
| WO | WO-2015035190 A1 | 3/2015 |
| WO | WO-2015081085 A2 | 6/2015 |

OTHER PUBLICATIONS

Meyer & Holz, Eye 25:661-672 (Year: 2011).*
Hicks, Martin J., et al., "Anti-Epidermal Growth Factor Receptor Gene Therapy for Glioblastoma", PLoS One 11(10): e0162978, (2016), 15 pgs.
"U.S. Appl. No. 16/664,835, Examiner Interview Summary mailed Nov. 15, 2022", 2 pgs.
"U.S. Appl. No. 16/664,835, Final Office Action mailed Jun. 29, 2022", 10 pgs.
"U.S. Appl. No. 16/664,835, Non Final Office Action mailed Mar. 3, 2022", 11 pgs.
"U.S. Appl. No. 16/664,835, Response filed Jun. 3, 2022 to Non Final Office Action mailed Mar. 3, 2022", 7 pgs.
"U.S. Appl. No. 16/664,835, Response filed Sep. 13, 2022 to Final Office Action mailed Jun. 29, 2022", 7 pgs.
Goedert, Michel, et al., "Epitope mapping of monoclonal antibodies to the paired helical filaments of Alzheimer's disease: identification of phosphorylation sites in tau protein", Biochem. J. vol. 301, 871-877, (1994), 7 pgs.
Rosenberg, et al., "AAVrh. 10-mediated expression of an anti-cocaine antibody mediates persistent passive immunization that suppresses cocaine-induced behavior", Human Gene Therapy, vol. 23, (2012), 451-459.
Sawamura, Naoya, et al., "Site-specific Phosphorylation of Tau Accompanied by Activation of Mitogen-activated Protein Kinase (MPAK) in Brains of Niemann-Pick Type C Mice", J. Biol. Chem., vol. 276, No. 13, Issue of Mar. 30, pp. 10314-10319, (2000), 6 pgs.
"Anti-CMV coat protein monoclonal antibody CymMV-L 23 immunoglobulin light chain variable region [Mus musculus]", Genbank Accession: AAT74922.1 [online]. Retrieved from the Internet: <URL: https://www.ncbi.nlm.nih.gov/protein/50346342>, (Jul. 21, 2004), 2 pgs.
"Anti-PRSV coat protein monoclonal antibody PRSV-H 10-9 immunoglobulin heavy chain variable region [Mus musculus]", GenBank Accession: AAT74919.1 [online]. Retrieved from the Internet: <URL: https://www.ncbi.nlm.nih.gov/protein/AAT74919.1>, (Jul. 21, 2004), 2 pgs.
"U.S. Appl. No. 14/426,347, Non Final Office Action mailed Jul. 21, 2016", 14 pgs.
"U.S. Appl. No. 14/426,347, Advisory Action malled Jul. 8, 2019", 4 pgs.
"U.S. Appl. No. 14/426,347, Appeal Brief filed Mar. 13, 2020".
"U.S. Appl. No. 14/426,347, Examiner Interview Summary mailed Oct. 26, 2017", 4 pgs.
"U.S. Appl. No. 14/426,347, Final Office Action mailed Jan. 12, 2017", 15 pgs.
"U.S. Appl. No. 14/426,347, Final Office Action mailed Feb. 15, 2018", 19 pgs.
"U.S. Appl. No. 14/426,347, Final Office Action mailed Mar. 14, 2019", 12 pgs.
"U.S. Appl. No. 14/426,347, Non Final Office Action mailed Aug. 16, 2017", 18 pgs.
"U.S. Appl. No. 14/426,347, Non Final Office Action mailed Sep. 12, 2018", 20 pgs.
"U.S. Appl. No. 14/426,347, Notice of Allowance mailed Mar. 30, 2020", 11 pgs.
"U.S. Appl. No. 14/426,347, Pre-Appeal Brief filed Aug. 14, 2019", 5 pgs.
"U.S. Appl. No. 14/426,347, Preliminary Amendment filed Mar. 5, 2015", 6 pgs.
"U.S. Appl. No. 14/426,347, Response filed Feb. 12, 2019 to Non Final Office Action mailed Sep. 12, 2018", 9 pgs.
"U.S. Appl. No. 14/426,347, Response filed Jun. 14, 2019 to Final Office Action mailed Mar. 14, 2019", 7 pgs.
"U.S. Appl. No. 14/426,347, Response filed Jun. 20, 2016 to Restriction Requirement mailed Apr. 14, 2016", 6 pgs.
"U.S. Appl. No. 14/426,347, Response filed Jul. 12, 2017 to Final Office Action mailed Jan. 12, 2017", 9 pgs.
"U.S. Appl. No. 14/426,347, Response filed Oct. 18, 2016 to Final Office Action mailed Jul. 21, 2016", 9 pgs.
"U.S. Appl. No. 14/426,347, Response filed Dec. 15, 2017 to Non Final Office Action mailed Aug. 16, 2017", 11 pgs.
"U.S. Appl. No. 14/426,347, Response Filed Aug. 9, 2018 to Final Office Action mailed Feb. 15, 2018", 13 pgs.
"U.S. Appl. No. 14/426,347, Restriction Requirement mailed Apr. 14, 2016", 7 pgs.
"U.S. Appl. No. 14/426,347, Supplemental Notice of Allowability mailed Jun. 10, 2020", 3 pgs.
"U.S. Appl. No. 14/911,400, Advisory Action mailed Jul. 24, 2017", 5 pgs.
"U.S. Appl. No. 14/911,400, Examiner Interview Summary mailed Aug. 26, 2019", 3 pgs.
"U.S. Appl. No. 14/911,400, Final Office Action malled Mar. 9, 2017", 20 pgs.
"U.S. Appl. No. 14/911,400, Final Office Action mailed May 7, 2018", 14 pgs.
"U.S. Appl. No. 14/911,400, Non Final Office Action mailed May 1, 2019", 12 pgs.
"U.S. Appl. No. 14/911,400, Non Final Office Action mailed Nov. 28, 2016", 18 pgs.
"U.S. Appl. No. 14/911,400, Non Final Office Action mailed Nov. 30, 2017", 13 pgs.
"U.S. Appl. No. 14/911,400, Preliminary Amendment filed Feb. 10, 2016", 7 pgs.
"U.S. Appl. No. 14/911,400, Respnse filed Jul. 12, 2017 to Final Office Action mailed Mar. 9, 2016", 11 pgs.
"U.S. Appl. No. 14/911,400, Response filed Feb. 15, 2017 to Non Final Office Action mailed Nov. 28, 2016", 10 pgs.
"U.S. Appl. No. 14/911,400, Response filled Nov. 2, 2016 to Restriction Requirement mailed Oct. 17, 2016", 7 pgs.
"U.S. Appl. No. 14/911,400, Response filed Nov. 7, 2018 to Final Office Action mailed May 7, 2018", 10 pgs.
"U.S. Appl. No. 14/911,400, Response filed Apr. 9, 2018 to Non Final Office Action mailed Nov. 30, 2017", 9 pgs.
"U.S. Appl. No. 14/911,400, Restriction Requirement mailed Oct. 17, 2016", 9 pgs.
"International Application Serial No. PCT/US2013/059674, International Search Report mailed Dec. 9, 2013", 4 pgs.
"International Application Serial No. PCT/US2013/059674, Written Opinion mailed Dec. 9, 2013", 4 pgs.
"International Application Serial No. PCT/US2014/054325, International Preliminary Report on Patentability mailed Mar. 17, 2016", 10 pgs.
"International Application Serial No. PCT/US2014/054325, International Search Report mailed Jan. 8, 2015", 7 pgs.
"International Application Serial No. PCT/US2014/054325, Written Opinion mailed Jan. 8, 2015", 9 pgs.
"International Application Serial No. PCTUS2013059674, International Preliminary Report on Patentability mailed Mar. 26, 2015", 4 pgs.
Cohen, et al., "", Oncologist 14: 1131-38, (2009).
Allal, Boutajangout, et al., "Passive immunization targeting pathological phospho-tau protein in a mouse model reduces functional decline and clears tau aggregates from the brain", Journal of Neurochemistry, vol. 118, No. 4, (Aug. 1, 2011), 658-667.
Almagro, Fransson, "", Frontiers in Bioscience, (2008).
Asokan, Aravind, et al., "The AAV Vector Toolkit: Poised at the Clinical Crossroads", Molecular Therapy, vol. 20, No. 4, (Apr. 2012), 699-708.
Asuni, Ayodeji A., et al., "Immunotherapy Targeting Pathological Tau Conformers in a Tangle Mouse Model Reduces Brain Pathology with Associated Functional Improvements", The Journal of Neuroscience, 27(34):, (2007), 9115-9129.

(56) References Cited

OTHER PUBLICATIONS

Barbero, S., et al., "Stromal Cell-derived Factor 1a Stimulates Human Glioblastoma Cell Growth through the Activation of Both Extracellular Signal-regulated Kinases 1/2 and Akt", Can Res., 63, (2003), 1969-1974.
Beibor, et al., "", Journal of Molecular Biology, (2000), 17 pgs.
Bittencourt, Chester, et al., "Anti-phospho-tau Gene Therapy for Chronic Traumatic Encephalopathy", Human Gene Therapy, DOI: 10.1089/hum.2019.174, 33 (2019).
Blanchetot, C., et al., "Neutralizing Nanobodies Targeting Diverse Chemokines Effectively Inhibit Chemokine Function", J. Biol Chem., 288(35), (2013), 25173-25182.
Boockvar, J. A., et al., "Safety and maximum tolerated dose of superselective intraarterial cerebral infusion of bevacizumab after osmotic blood-brain barrier disruption for recurrent malignant glioma. Clinical article.", J. Neurosurg., 114(3), (2011), 624-632.
Boutajangout, "Immunotherapy targeting pathological tau prevents cognitive decline in a new tangle mouse model", Supplemental Figures, The Journal of Neuroscience, 30(49), (2010), 5 pgs.
Boutajangout, Allal, et al., "Immunotherapy Targeting Pathological Tau Prevents Cognitive Decline in a New Tangle Mouse Model", The Journal of Neuroscience, 30(49), (2010), 16559-16566.
Boutajangout, Allal, et al., "Passive immunization targeting pathological phospho-tau protein in a mouse model reduces functional decline and clears tau aggregates from the brain", Journal of Neurochemistry, 118(4), (2011), 658-667.
Boutajangout, Allal, et al., "Tau-Based Therapeutic Approaches for Alzheimer's Disease—A Mini-Review", Gerontology; 60, (2014), 381-385.
Bright, Jessica, et al., "Human secreted tau increases amyloid-beta production", Neurobiology of Aging, 36, (2015), 693e709.
Cardinale, A, "The potential of intracellular antibodies for therapeutic targeting of protein-misfolding diseases", Trends in Molecular Medicine, Elsevier Current Trends, GB, vol. 14, No. 9, (Sep. 1, 2008), 373-380.
Chai, Xiyun, et al., "Passive Immunization with Anti-Tau Antibodies in Two Transgenic Models", The Journal of Biological Chemistry, 286(39), (2011), 34457-34467.
Choi, et al., "", Molecular BioSystems, (2011).
Chothia, Cyrus, et al., "Canonical Structures for the Hypervariable Regions of Immunoglobulins", J. Mol. Biol., 196, (1987), 901-917.
De, Bishnu P., et al., "High Levels of Persistent Expression of alpha1-Antitrypsin Mediated by the Nonhuman Primate Serotype rh. 10 Adeno-associated Virus Despite Preexisting Immunity to Common Human Adeno-associated Viruses", Mol. Ther., 13(1), (Jan. 2006), 67-76.
Deborah, Ryan A, et al., "A[beta]-directed Single-chain Antibody Delivery Via a Serotype-1 AAV Vector Improves Learning Behavior and Pathology in Alzheimer's Disease Mice", Molecular Therapy, vol. 18, No. 8,, (Jun. 15, 2010), 1471-1481.
Fang, J, "Stable antibody expression at therapeutic levels using the 2A peptide", Nature Biotechnology, Nature Publishing Group, New York, NY, US, vol. 23, No. 5, (Apr. 17, 2005), 584-590.
Fukuchi, K I, et al., "Anti-Abeta single-chain antibody delivery via adeno-associated virus for treatment of Alzheimer's disease", Neurobiology of disease, blackwell Scientific Publications, Oxford, GB, vol. 23, No. 3, (Sep. 1, 2006), 502-511.
Griffits, et al., "", The EMBO Journal, (1993).
Gupta, et al., "Development of an EGFRvIII specific recombinant antibody", BMC Biotech., 10, (2010), 1-13.
Harding, T. C., et al., "AAV Serotype 8-Mediated Gene Delivery of a Soluble VEGF Receptor to the CNS for the Treatment of Glioblastoma", Mol. Ther., 13(5), (May 2006), 956-966.
Hicks, Martin J., et al., "Anti-Epidermal Growth Factor Receptor Gene Therapy for Glioblastoma", PLoS One 11(10): e0162978. https://doi.org/10.1231/journal.pone.0162978, (Oct. 6, 2016), 1-11.
Hicks, Martin J., et al., "Genetic Modification of Neurons to Express Bevacizumab for Local Anti-angiogenesis Treatment of Blioblastoma", Cancer Gene Ther. Jan. 2015; 22(1): 1-8. doi:10.1038/cgt.2014.58, HHS Public Access, Author manuscript, (2015), 20.
Jicha, G A, et al., "Alz-50 and mc-1, a New monoclonal antibody raised to paired helical filaments, recognize conformational epitopes on recombinant tau", Journal of Neuroscience Research, Wiley-Liss, us, vol. 48, No. 2, (Apr. 15, 1997), 128-132.
Kunik, Vered, et al., "Paratome: an online tool for systematic identification of antigen-binding regions in antibodies based on sequence or structure", Nucleic Acids Research, vol. 40, Issue W1, (2012), W521-W524.
Lee, Seung-Hye, et al., "Antibody-Mediated Targeting of Tau In Vivo Does Not Require Effector Function and Microglial Engagement", Cell Reports, 16, (2016), 1690-1700.
Lefranc, Marie-Paule, et al., "IMGT unique numbering for immunoglobulin and T cell receptor variable domains and Ig superfamily V-like domains", Developmental & Comparative Immunology, 27, (2003), 55-77.
Lefranc, Marie-Paule, "IMGT, the international ImMunoGeneTics database: a high-quality information system for comparative immunogenetics and immunology", Developmental and Comparative Immunology, 26, (2002), 697-705.
Levites, Y, et al., "Intracranial Adeno-Associated Virus-Mediated Delivery of Anti-Pan Amyloid beta, Amyloid beta40, and Amyloid beta42 Single-Chain Variable Fragments Attenuates Plaque Pathology in Amyloid Precursor Protein Mice", Journal of Neuroscience, vol. 26, No. 46, (Nov. 15, 2006), 11923-11928.
Liu, Wencheng, et al., "Victored Intracerebral Immunization witht eh Anti-Tau Monoclonal Antibody PHF1 Markedly Reduces Tau Pathology in Mutant Tau Transgenic Mice", The Journal of Neuroscience, Dec. 7, 2016 36(49):12425-12435, Neurobiology of Disease, (2016).
Magdelaine-Beuzelin, Charlotte, et al., "Structure-function relationships of the variable domains of monoclonal antibodies approved for cancer treatment", Crit. Rev. Hematol., 64(3), (2007), 210-225.
Martens, et al., "Clin. Cancer", (2008), 5447-5458.
Nakamura, Kazuhiro, et al., "Proline Isomer-Speci?c Antibodies Reveal the Early Pathogenic Tau Conformation in Alzheimer's Disease", Cell, 149, (2012), 232-244.
Normano, N., et al., "Target-based agents against ErbB receptors and their ligands: a novel approach to cancer treatment", Endocrine-Related Cancer, 10, (2003), 1-21.
Pagovich, Odelya E., et al., "Anti-higE gene therapy of peanut-induced anaphylaxis in a humanized murine model of peanut allergy", J. Allergy Clin. Immunol., 138, (2016), 1652.
Pope, W. B., et al., "Patterns of progression in patients with recurrent glioblastoma treated with bevacizumab.", Neurology, 76(5), (2011), 432-437.
Ramos, T. C., et al., "Treatment of High-Grade Glioma Patients with the humanized Anti-Epidermal Growth Factor Receptor (EGFR) Antibody h-R3: Report from a Phase I/II Trial", Cancer Biol Ther., 5(4), (Apr. 2006), 375-379.
Rudikoff, et al., "Single amino acid substitution altering antigen-binding specificity", Proc Natl Acad Sci USA 79(6), (Mar. 1982), 1979-83.
Saif, M. W., "Anti-VEGF agents in metastatic colorectal cancer (mCRC): are they all alike?", Cancer Mangement and Res., 5, (2013), 103-115.
Schroeder, S., "Intracranial Administration of Antibodies Directed Against Tau: A Potential Therapy for Alzheimer's Disease", Abstracts for the 19th Annual Meeting of the American Society for Neural Therapy and Repair Cell Transplantation, vol. 21, (2012), p. 789.
Sofer-Podesta, C., et al., "Adenovirus-Mediated Delivery of an Anti-V Antigen Monoclonal Antibody Protects Mice against a Lethal Yersinia pestis Challenge", Infect. Immun., 77(4), (2009), 1561-1568.
Sondi, D., et al., "AAV2-mediated CLN2 gene transfer to rodent and non-human primate brain results in long-term TPP-I expression compatible with therapy for LINCL", Gene Ther., 12(22), (2005), 1618-1632.
Sondi, D., et al., "Enhanced Survival of the LINCL Mouse Following CLN2 Gene Transfer Using the rh.10 Rhesus Macaque-derived Adeno-associated Virus Vector", Mol Ther, 15(3), (2007), 481-491.

(56) References Cited

OTHER PUBLICATIONS

Souweidane, M. M., et al., "Gene therapy for late infantile neuronal ceroid lipofuscinosis: neurosurgical considerations", J. Neurosurg. Pediatrics, 6(2), (2010), 115-122.

Sudol, K L, et al., "Generating differentially targeted amyloid-beta specific intrabodies as a passive vaccination strategy for Alzheimer's disease", Molecular Therapy, Nature Publishing Group, GB, vol. 17, No. 12, (Dec. 1, 2009), 2031-2040.

Wang, Y J, et al., "Intramuscular delivery of a single chain antibody gene reduces brain Abeta burden in a mouse model of Alzheimer's disease", Neurobiology of Aging, Tarrytown, NY, US, vol. 30, No. 3, (Mar. 1, 2009), 364-376.

Whiteside, Theresa L., et al., "Emerging Opportunities and Challenges in Cancer Immunotherapy", Clin Cancer Res 2016; 22:1845-1855, www.aacrjournals.org; Downloaded from clincancerres. aacrjournals.org on Jul. 16, 2018 American Association for Cancer Research, (2018), 1845-1856.

Worgall, Stefan, et al., "Treatment of Late infantile Neuronal Ceroid Lipofuscinosis by CNS Administration of a Serotype 2 Adeno-Associated Virus Expressing CLN2 cDNA.", Human Gene Therapy, 19(5), (2008), 463-474.

Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.

X, Chai, et al., "Passive Immunization with Anti-Tau Antibodies in Two Transgenic Models: Reduction of Tau Pathology and delay of Disease Progression", Journal of Biological Chemistry, vol. 286, No. 39, (Sep. 30, 2011), 34457-34467.

Zhong, C., et al., "Development and Preclinical Characterization of a Humanized Antibody Targeting CXCL12", Clin Can. Res., 19, (2013), 4433-4445.

Zhu, et al., "A Unique and Conserved Neutralization Epitope in H5N1 Influenza Viruses Identified by an Antibody against the A/Goose/Guangdong/1/96 Hemagglutinin", Journal of Virology, 87(23), (2013), 12619-12635.

"U.S. Appl. No. 16/664,835, Final Office Action mailed May 23, 2023", 8 pgs.

"U.S. Appl. No. 16/664,835, Response filed May 1, 2023 to Non Final Office Action mailed Feb. 1, 2023", 7 pgs.

Alam, et al., "Strategy for effective brain drug delivery", European Journal of Pharmaceutical Sciences, vol. 40, (2010), 385-403.

Cearley, et al., "Transduction characteristics of adeno-associated virus vectors expressing cap serotypes 7, 8, 9, nd Rh10 in the mouse brain", Molecular Therapy, vol. 13, (2006), 528-537.

Hicks, M. J., et al., "AAV-Directed Persistent Expression of a Gene Encoding Anti-Nicotine Antibody for Smoking Cessation", Sci. Transl. Med., 4(140): 140ra87, (2012), 1-7.

Mao, Yanxiong, et al., "Persistent Suppression of Ocular Neovascularization with Intravitreal Administration of AAVrh.10 Coding for Bevacizumab", Human Gene Ther., 22(12), (2011), 1525-1535.

Ryan, Deborah A, et al., "AB-directed Single-chain Antibody Delivery Via a Serotype-1 AAV Vector Improves Learning Behavior and Pathology in Alzheimer's Disease Mice", vol. 18, Molecular Therapy, (2010), 1471-1481.

Shimada, et al., "Prophylaxis and treatment of Alzheimer's disease by delivery of an adeno-associated virus encoding a monoclonal antibody targeting the amyloid beta protein", PLOS One, vol. 8, issue 3, (2013), 1-8.

Wang, Guoqing, et al., "Persistent Expression of Biologically Active Anti-HER2 Antiboy by AAVrh.10-mediated Gene Transfer", Cancer Gene Ther., 17(8), (2010), 559-570.

Watanabe, M., et al., "AAVrh.10-mediated genetic delivery of bevacizumab to the pleura to provide local anti-VEGF to suppress growth of metastatic lung tumors", Gene Therapy, 17(8), (2010), 1042-1051.

"U.S. Appl. No. 16/664,835, Advisory Action mailed Aug. 10, 2023", 4 pgs.

"U.S. Appl. No. 16/664,835, Response filed Jul. 21, 2023 to Final Office Action mailed May 23, 2023", 8 pgs.

"U.S. Appl. No. 16/664,835, Response filed Sep. 21, 2023 to Advisory Action mailed Aug. 10, 2023", 9 pgs.

Arslan, et al., "Astrocytoma", Sci. Rep., 12:5449 (2020), Astrocytoma | Brain and spinal cord tumours | Cancer Research UK, (2020), 5449.

Arslan, Merve, et al., "Effect of non-repetitive linker on in vitro and in vivo properties of an anti-VEGF scFv", Scientific Reports, (2022) 12:5449., <https://doi.org/10.1038/s41598-022-09324-4>, (Mar. 31, 2022), 8 pgs.

Bahmad, Hisham F., et al., "Colonic Ganglioneuroma: A Combined Single-Institution Experience and Review of the Literature of Forty-Three Patients", Diseases, 11:69, (2023).

Hughes, Chris, et al., "AAV2/8 Anti-angiogenic Gene Therapy Using Single-Chain Antibodies Inhibits Murine Choroidal Neovascularization", Molecular Therapy: Methods & Clinical Development vol. 13, Jun. 2019., <http://www.moleculartherapy.org/>, (Jun. 2019), 16 pgs.

Perry, Arie, et al., "Malignant Gliomas with Primitive Neuroectodermal Tumor-like Components: A Clinicopathyologic and Genetic Study of 53 Cases", Brain Pathol, 19(1), (2009), 81-90.

Sim, et al., "Neurocytoma is a Tumor of Adult Neuronal Progenitor Cells", The Journal of Neuroscience, Nov. 29, 2006 26(48):12544-12555.

Single Use Support, Pioneering Biopharma, "3 Examples of FDA approved AAVs ingene therapy", Single Use Support, Pioneering Biopharma, 2023., <https://www.susupport.com/knowledge/viral-vectors/approved-aav-gene-therapy>, (Sep. 19, 2023), 8 pgs.

Van Den Bent, Marin J., et al., "Oligodendrogliome", Oligodendroglioma—PubMed; Crit. Rev. Oncol. Hematol., 66:262, (2008), 1.

"U.S. Appl. No. 16/664,835, Non Final Office Action mailed Jan. 25, 2024", 22 pgs.

"Tabel filed on Dec. 15, 2017 in U.S. Appl. No. 14/426,347", 1.

"U.S. Appl. No. 16/664,835, Response filed Apr. 29, 2024 to Non Final Office Action mailed Jan. 25, 2024", 9 pgs.

"U.S. Appl. No. 16/664,835, Final Office Action mailed Aug. 21, 2024", 17 pgs.

Castillo-Carranza, Diana L., "Tau aggregates as immunotherapeutic targets", Frontiers in Bioscience, Scholar, 5, 426-438, Jan. 1, 2013, (2013), 426-438.

Madeo, Jennifer, "Alzheimer's Disease and Immunotherapy", Aging and Disease, vol. 4, No. 4; 210-220, Aug. 2013, www.aginganddisease.org; Department of Medicinet, Nassau University Medical Center, East Meadow, NY 11554, USA, (2013), 210-220.

Rocha, "Targeted drug delivery across the blood brain barrier in Alzheimer's disease", Curr Pharm Des. 2013;19 (37): 6635-46, National Center for Biotechnology Information (NCBI) at the U.S. National Library of Medicine (NLM), (2013), 1.

Sacramento, Chester Bittenbourt, "Anti-Phospho-Tau Gene Therapy for Chronic Traumatic Encephalopathy", Human Gene Therapy, vol. 31, Nos. 1 and 2, 2020 by Mary Ann Liebert, Inc.; DOI: 10.1089 hum.2019.174, (2020), 57-72.

\* cited by examiner

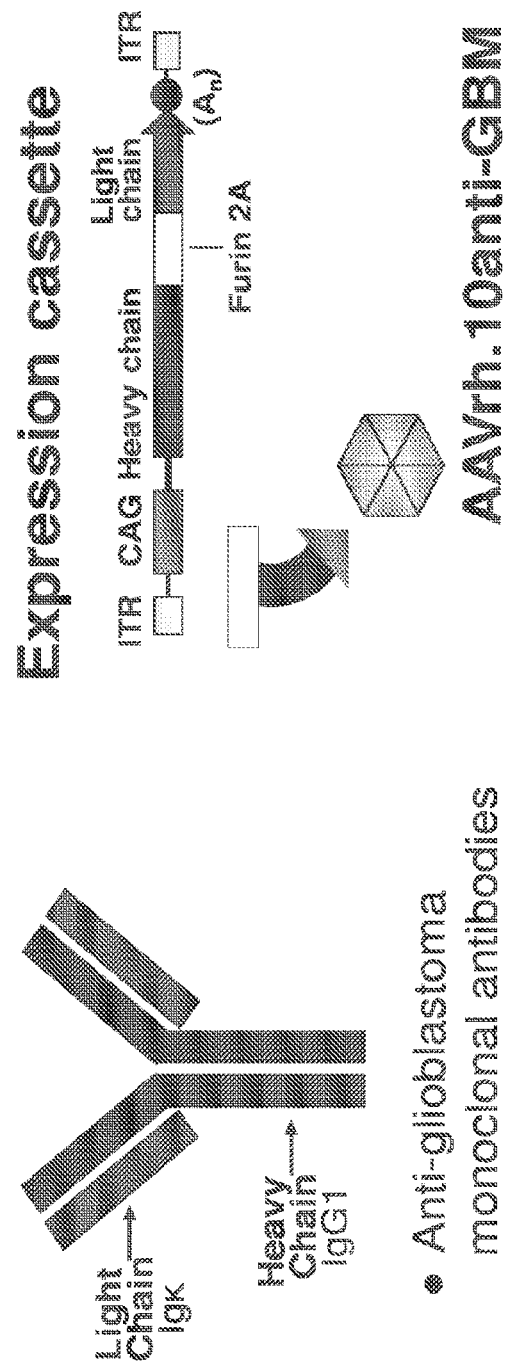

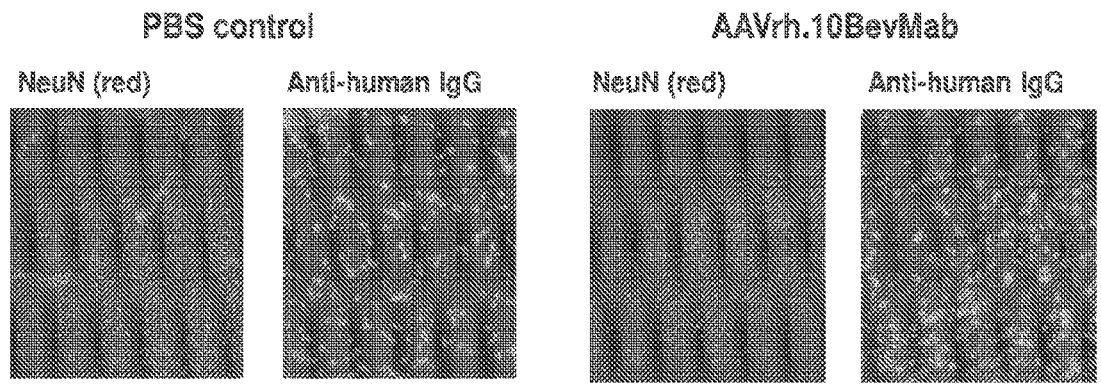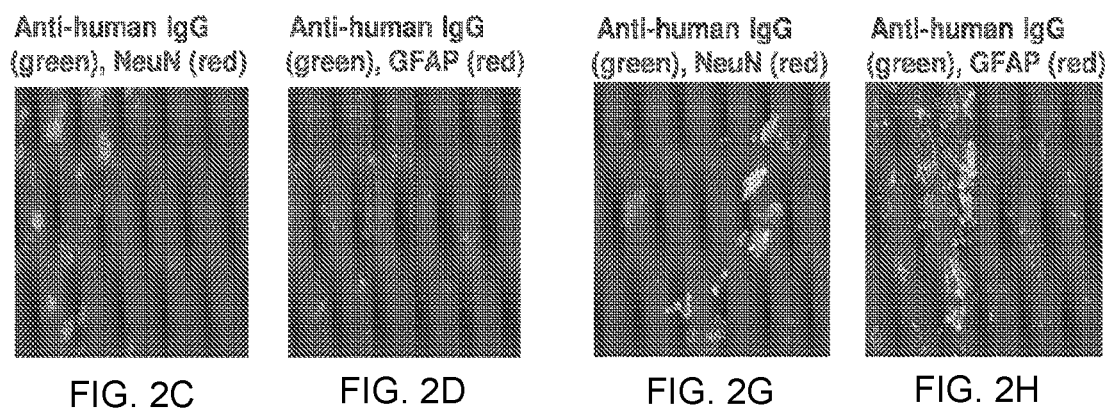

TREATMENT OF BRAIN CANCERS USING CENTRAL NERVOUS SYSTEM MEDIATED GENE TRANSFER OF MONOCLONAL ANTIBODIES

CROSS-REFERENCE TO RELATED APPLICATIONS

This application is a continuation of U.S. application Ser. No. 14/426,347, filed Mar. 5, 2015, which is a U.S. national stage application under 35 U.S.C. § 371 of PCT/US2013/059674, filed Sep. 13, 2013, and published as WO 2014/043480 A1 on Mar. 20, 2014, which claims the benefit of the filing date of Ser. No. 61/700,599, filed Sep. 13, 2012; which applications and publication are incorporated by reference as if reproduced herein and made a part hereof in their entirety, and the benefit of priority of each of which is claimed herein.

BACKGROUND

Glioblastoma multiforme (GBM), the most common central nervous system (CNS) malignancy (Louis at al., 2007; Van Meir at al., 2010; Dolecek at al., 2012), is an aggressive human cancer, with a median survival of only 14 months (Louis at al., 2007; Van Meir at al., 2010; Dolecek at al., 2012). Current therapy is surgery plus radiation, but the invasive growth of the tumor prevents complete removal. Moreover, GBM is typically radioresistant (Barker et al., 1998; Allahdini et al., 2010; Park et al., 2010) and GBM tumors may also acquire resistance to chemotherapy (Nagasawa et al., 2012; Chaudhyr at al., 2013). Although a great deal is known about the aberrant biology exhibited by GBM, applying therapies against these biologic processes is limited by the blood-brain barrier (BBB), which restricts many systemically administered therapies from reaching the brain parenchyma, including anti-cancer monoclonal antibodies (Wang et al., 2010; Knizetova et al., 2008; Thompson at al., 2011; Boockvar et al., 2011; Adamson et al., 2009; Jain et al., 2007). For example, based on the knowledge that GBM tumors are highly vascular and express high levels of the angiogenic mediator vascular endothelial growth factor (VEGF), there have been several clinical studies of systemically administered anti-VEGF monoclonal antibodies, but the results have been disappointing, with little effect on extending survival from GBM (Thompson et al., 2011; Sweet et al., 2012).

SUMMARY OF THE INVENTION

The invention relates to delivery of therapeutic molecules including antibodies to the central nervous system, for example, to treat cancer. To bypass the BBB, in one embodiment, administration of gene transfer vectors, e.g., adeno-associated virus (AAV) gene transfer vectors, to the central nervous system (CNS) was employed to deliver genetic sequences encoding therapeutic monoclonal antibodies that modify normal CNS cells to chronically deliver those monoclonal antibodies to the local milieu.

In one approach, as much of a central nervous system tumor as possible is surgically removed and then a gene therapy vector encoding a therapeutic molecule, such as a therapeutic antibody, is administered to one or more areas in and/or near the site of the excised tumor and/or to other areas of the central nervous system amenable to gene delivery and expression. In another strategy, as much of a central nervous system tumor is surgically removed and subsequently, e.g., hours, days or weeks after the surgery, a gene therapy vector encoding a therapeutic molecule, such as a therapeutic antibody, is administered to one or more areas in and/or near the site of the excised tumor and/or to other areas of the central nervous system amenable to gene delivery and expression. Because neurons do not turn over, the expression of the therapeutic molecule is persistent, an important feature in treating central nervous systems cancers such as GBM, where it is generally not feasible to surgically remove the entire tumor. The gene therapy vector may be delivered to cells in the central nervous system via any suitable vehicle, e.g., viral vectors or non-viral vectors such as plasmid DNA, liposomes, microparticles, nanoparticles, lipoplexes, polyplexes, nanotubes, and the like. In one embodiment, the vector selected for administration mediates CNS expression, e.g., specifically in neurons. For example, an adeno-associated virus (AAV) vector with specificity for neurons (infection of and expression in neurons) may be employed (Sondhi et al., 2007; Sondhi et al., 2012; Worgall et al., 2008; Souweidane et al., 2010).

To test this approach, AAVrh.10BevMab, an AAVrh.10-based vector coding for bevacizumab (Avastin®), an anti-vascular endothelial growth factor (VEGF) monoclonal antibody, was administered to the CNS of NOD/SCID immunodeficient mice in which GBM xenografts (e.g., from the U87MG human GBM line) were implanted in the striatum. ELISA and Western analysis showed localized expression of the bevacizumab monoclonal in the area of the striatum (60-110 pg/µg total protein), and immunohistochemistry demonstrated the expression of the monoclonal in the local area of administration. Gd-DTPA enhanced magnetic resonance imaging (MRI) imaging of the brains of AAVrh.10BevMab-treated and non-treated mice was used to quantify tumor growth. Delivery of AAVrh.10BevMab vector to the striatum reduced the average tumor growth of the GBM xenograft by greater than 5-fold at 18 days (non-treated 9.6±12.7 mm³, treated 1.7±10.5 mm³, p<0.02) and T1 pre- and post-Gd-DTPA MRI analysis of mouse brains showed greater Gd-DTPA tumor enhancement (e.g., more blood flow and infiltrating tumor) in non-treated mice (74.6±26.7%) compared to treated mice (3.2±2.7%, p<0.02). Further, treatment with AAVrh.10BevMab increased the median survival time of mice with GBM xenografts by 31.2% (treated 47.3±2.8 days versus non-treated, 32.5±2.4 days; p<9×10⁻⁵). The data demonstrate that CNS genetic delivery of therapeutic monoclonal antibodies suppresses the CNS growth of human GBM in immunodeficient mice. The data also show that AAVrh.10BevMab mediates expression of monoclonal antibodies, such as bevacizumab, in CNS neurons, and reduces GBM tumor burden as shown by histology, MRI and increased survival. Thus, local gene transfer-mediated CNS therapy, e.g., anti-angiogenesis therapy, may be a useful strategy to treat glioblastoma and other central nervous system tumors.

One aspect of the invention is thus a method for treating or inhibiting cancer of the central nervous system in an animal, e.g., a mammal such as a human. The method includes administering to the animal, e.g., a mammal, an expression vector encoding an antibody or non-antibody ligand in an amount effective to treat or inhibit the cancer in the animal. The vector that is administered may encode an antibody including but not limited to an anti-VEGF antibody, e.g., the FDA-approved Bevacizumab antibody, or any of the antibodies described in U.S. Pat. Nos. 6,054,297 and 5,821,337, an anti-VEGF receptor (VEGFR) antibody, an anti-epidermal growth factor receptor (EGFR) antibody, an anti-CXCR4 antibody, or an anti-CXCL12 (SDF-1) antibody, or may encode a non-antibody antagonistic ligand of VEGFR, e.g., of VEGFR-2, a non-antibody antagonistic ligand of EGFR, or a non-antibody antagonistic ligand of CXCR4.

In one embodiment, the method includes administering to the animal, e.g., a mammal, an expression vector encoding an antibody directed against VEGF or against VEGFR in an amount effective to treat or inhibit the cancer in the animal. In one aspect, the antibody may be an anti-VEGF antibody that specifically binds to VEGF, e.g., to VEGF-A, specifically binds to human VEGF but not murine VEGF, or specifically binds to VEGFR, e.g., to VEGFR-2. Treatment with such an expression vector that encodes an anti-VEGF antibody or an anti-VEGFR antibody can be combined with other anti-cancer agents and/or pain medications. The cancer that is treated or inhibited can be a central nervous cancer such as a glioblastoma (e.g., glioblastoma multiforme (GBM)), a glial tumor, astrocytoma, and also related neural and glial tumors, which include grades 1 and 2 glioma, oligodendroglioma, neurocytoma, dysplastic neuroepithelial tumor, primitive neuroectodermal tumor, ganglioneuroma, and combinations thereof. In some embodiments, the cancer that is treated is glioblastoma, including malignant glioblastoma multiforme. The animal treated may be a human, domesticated animal, e.g., a canine, feline, bovine, equine, caprine, ovine or swine, experimental animal or a zoo animal. In some embodiments, the vector is administered locally. In other embodiments, the vector is administered systemically (e.g., orally or parenterally).

Another aspect of the invention is a method for treating or inhibiting cancer of the central nervous system in an animal, e.g., a mammal, that includes administering to the animal an expression vector encoding an antibody directed against CXCL12 (an anti-CXCL12 antibody) or an anti-CXCR4 antibody in an amount effective to treat or inhibit the cancer in the animal. In one aspect, the antibody may be an anti-CXCL12 antibody that specifically binds to CXCL12. Treatment with an expression vector that encodes an anti-CXCL12 antibody or an anti-CXCR4 antibody can be combined with other anti-cancer agents and/or pain medications. The cancer that is treated or inhibited can be a central nervous cancer such as a glioblastoma (e.g., glioblastoma multiforme (GBM)), a glial tumor, astrocytoma, and also related neural and glial tumors, which include grades 1 and 2 glioma, oligodendroglioma, neurocytoma, dysplastic neuroepithelial tumor, primitive neuroectodermal tumor, ganglioneuroma, and combinations thereof. In some embodiments, the cancer that is treated is glioblastoma, including malignant glioblastoma multiforme. The animal treated may be a human, domesticated animal, experimental animal or a zoo animal. In some embodiments, the vector is administered locally. In other embodiments, the vector is administered systemically (e.g., orally or parenterally).

Another aspect of the invention is a method for treating or inhibiting cancer of the central nervous system in an animal which includes administering to the animal an expression vector encoding an antibody directed against epidermal growth factor receptor (EGFR), e.g., a variant of EGFR such as EGFRvIII, in an amount effective to treat or inhibit the cancer in the animal. In one aspect, the antibody may be an anti-EGFR vIII antibody that specifically binds to EGFR vIII including but not limited to one having a tyrosine at H59 of CDRH2 and a tyrosine at H105 of CDRH3 or one that has a residue other than tyrosine at H59 of CDRH2 and/or a residue other than tyrosine at H105 of CDRH3, e.g., a phenylalanine at one or both of those residues. Treatment with such an expression vector that encodes an anti-EGFR antibody such as an anti-EGFR vIII antibody can be combined with other anti-cancer agents and/or pain medications. The cancer that is treated or inhibited can be a central nervous cancer such as a glioblastoma (e.g., glioblastoma multiforme (GBM)), a glial tumor, astrocytoma, and also related neural and glial tumors, which include grades 1 and 2 glioma, oligodendroglioma, neurocytoma, dysplastic neuroepithelial tumor, primitive neuroectodermal tumor, ganglioneuroma, and combinations thereof. In some embodiments, the cancer that is treated is glioblastoma, including malignant glioblastoma multiforme. The animal treated may be a human, domesticated animal, experimental animal or a zoo animal. In some embodiments, the vector is administered locally. In other embodiments, the vector is administered systemically (e.g., orally or parenterally).

In some embodiments, the methods can include combination antibody or non-antibody ligand treatments. For example, a further aspect of the invention is a method for treating or inhibiting cancer of the central nervous system in a mammal that includes administering to the mammal any combination of an expression vector or expression cassette encoding an antibody directed against VEGF; an expression vector encoding an antibody directed against CXCL12; or an expression vector encoding an antibody directed against EGFR (e.g., a mutant form of EGFR such as EGFRvIII), in an effective amount to treat or inhibit the cancer in the animal.

The expression vector can encode one, two or more types of antibodies (e.g., an anti-VEGF antibody, anti-CXCL12 antibody and/or anti-EGFR antibody) including antigen binding fragments thereof. The coding region for the antibody or antibodies can be placed in one or more expression cassette(s), e.g., a coding region for light and heavy chains for an antibody may be in the same or a different expression cassette. Such an expression cassette can be present in an expression vector. Suitable expression vectors include viral vectors such as an adeno-associated viral vector, including a neurotropic adeno-associated viral vector such as a neurotropic recombinant adeno-associated virus (rAAV) (see, e.g., Sofer-Podesta et al. (2009): Wang et al. (2010): Watanabe et al. (2008); European Patent Application EP0968724 by Anderson et al., and U.S. Pat. No. 7,456,015, each of which is specifically incorporated herein by reference in its entirety).

Central nervous system delivery of an AAV vector encoding an anti-VEGF antibody, anti-EGFR antibody or anti-CXCL12 antibody is applicable to delivery vehicles other than AAV and to other anti-tumor antibodies or antagonistic ligands for VEGFR, EGFR or CXCL4, in the treatment of glioblastoma and other malignancies within the central nervous system. Other viral vectors include but are not limited to lentiviral vectors, retroviral vectors, herpes virus vectors, e.g., cytomegalovirus vectors, herpes simplex virus vectors or varicella zoster virus vectors, adenovirus vectors, e.g., helper-dependent adenovirus vectors, adenovirus-AAV hybrids, rabies virus vectors, vesicular stomatitis virus (VSV) vectors, coronavirus vectors, poxvirus vectors and the like. Non-viral vectors may be employed to deliver the expression vectors, e.g., liposomes, nanoparticles, microparticles, lipoplexes, polyplexes, nanotubes, and the like. In one embodiment, two or more expression vectors are administered, for instance, each encoding a distinct antibody or antigen binding fragment thereof. In one embodiment, an expression vector with two or more expression cassettes is administered, for instance, each cassette encoding a distinct antibody or antigen binding fragment thereof.

Thus, the invention provides compounds for use in medical therapy, such as gene therapy vectors that inhibit or prevent angiogenesis, block or inhibit activation of EGFR, inhibit or prevent tumor cell invasion, decrease tumor burden, enhance survival, and/or inhibit metastases, optionally in conjunction with other compounds. Accordingly, the compounds of the invention are useful to inhibit or treat cancer, e.g., malignant gliomas or other proliferative diseases of the central nervous system. Also provided is the use of the compounds for the manufacture of a medicament to inhibit or prevent angiogenesis, block or inhibit activation of EGFR, inhibit or prevent invasion, decrease tumor burden, enhance survival, and/or inhibit metastases.

BRIEF DESCRIPTION OF THE FIGURES

FIGS. 1A-B. Construction and function of AAVrh.10BevMab. A) Schematic of AAV vector to express Bevacizumab. Bevacizumab is a humanized MAb specific for VEGF-A, e.g., binds to all major VEGF-A isoforms (121, 165, 189) and prevents activation of VEGF receptors VEGFR-1 (Flt-1) and VEGFR-2 (KDR). The expression cassette uses a promoter (CMV enhanced chicken β-actin) followed by a semi-synthetic gene encoding a polyprotein having of the heavy chain followed by a cleavable furin 2A sequence followed by the light chain. Self assembly of the expressed subunits occurs spontaneously after cleavage. B) AAV directed expression of Bevacizumab is specific for human VEGF.

DETAILED DESCRIPTION

Definitions

Figure 1B:
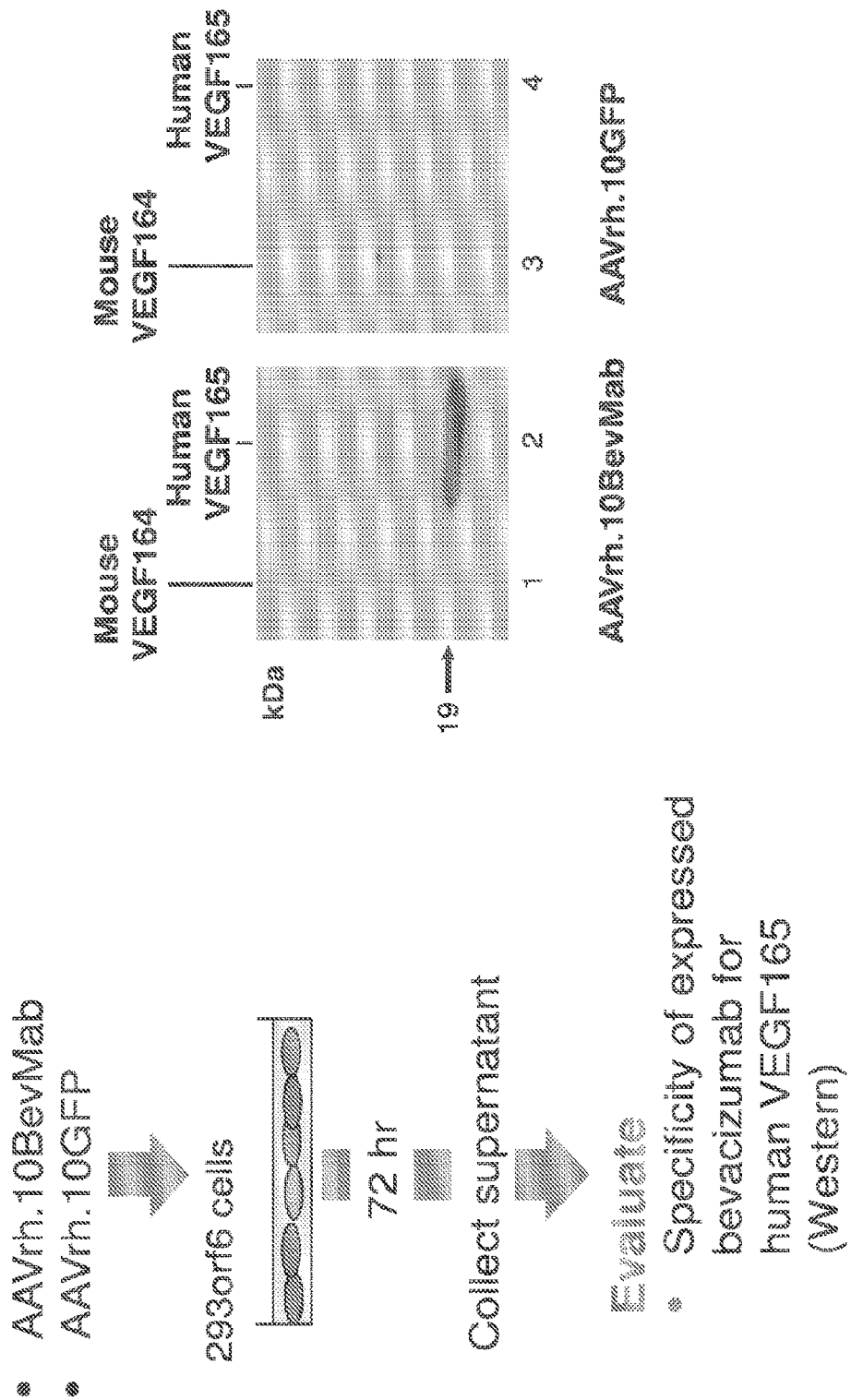

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus including helper-dependent adenovirus vectors, which do not express any adenovirus genes and are immunologically silent to allow for persistent expression, adeno-associated virus (AAV), adenovirus-AAV hybrid vectors, e.g., hybrids that have an AAV genome, e.g., an AAV-1, AAV-2, AAV-3, AAV-4, AAV-5, AAV-6, AAV-7, AAV-8, AAV-9, AAV-10, AAV-11 or AAV-12 genome, in an adenovirus capsid, poxvirus, papillomavirus, lentivirus, herpesvirus, foam virus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding such as RGD (Arg-Gly-Asp)); components that influence uptake of the vector nucleic acid by the cell; components that influence localization of the polynucleotide within the cell after uptake (such as agents mediating nuclear localization); and components that influence expression of the polynucleotide. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene"), e.g., via a recombinant virus, into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery or "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the cell if integrated into the genome or maintained extrachromosomally. Such a transgene may include a gene which is partly or entirely heterologous (i.e., foreign) to the transgenic host cell or organism, or may represent a gene homologous to an endogenous gene of the host cell or organism.

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight serotypes of primate AAVs, AAV-1 to AAV-8. For example, serotype AAV2 is used to refer to an AAV which contains capsid proteins encoded from the cap gene of AAV 2 and a genome containing 5' and 3' ITR sequences from the same AAV2 serotype. The abbreviation "rAAV" refers to recombinant adeno-associated virus, also referred to as a recombinant AAV vector (or "rAAV vector").

A cell has been "transformed", "transduced", "transfected" or "genetically modified" by exogenous or heterologous nucleic acids when such nucleic acids have been introduced inside the cell. Transforming DNA may or may not be integrated (covalently linked) with chromosomal DNA making up the genome of the cell. In mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication.

The term "wild-type" with respect to a gene or gene product refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" or "variant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

The term "control elements" refers collectively to promoter regions, polyadenylation stimulations, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a cleavable or targeting peptide sequence is operably linked to another protein if the resulting fusion is cleaved into two or more parts as a result of cleavable sequence or is transported into an organelle as a result of the presence of an organelle targeting peptide.

"Homology" refers to the percent of identity between two polynucleotides or two polypeptides. For example, polypeptides, e.g., antibodies, of the invention may have at least 50%, 55%, 60%, 65%, 70%, 75%, 80%, 85%, 90%, 92%, 95%, 96%, 97%, 98% or 99% amino acid sequence identity to a reference polypeptide sequence, for instance, a reference variable or constant region sequence of an antibody, e.g., have at least 50%, 55%, 60%, 65%, 70%, 75%, 80%, 85%, 90%, 92%, 95%, 96%, 97%, 98% or 99% amino acid sequence identity to any of SEQ ID Nos. 4-11. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, at least about 90%, or at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination stimulation, may also be included.

The term "exogenous," when used in relation to a protein, gene or nucleic acid, e.g., polynucleotide, in a cell or organism refers to a protein, gene, or nucleic acid which has been introduced into the cell or organism by artificial or natural means, or in relation to a cell refers to a cell which was isolated and subsequently introduced to other cells or to an organism by artificial or natural means (a "donor" cell). An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

The term "inked" in the context of polypeptide sequences includes a linkage introduced through recombinant means or chemical means. Linkers and methods of linking antibody fragments such as scFv and dsFv are described in WO 98/41641.

The terms "effective amount" or "amount effective to" or "therapeutically effective amount" refers to an amount sufficient to induce a detectable therapeutic response in the subject. Assays for determining therapeutic responses are well known in the art.

The terms "patient" or "subject" are used interchangeably and refer to a mammalian subject to be treated, for instance, a human patient. In some cases, the methods of the invention find use in experimental animals, in veterinary application, and in the development of animal models for disease, including, but not limited to, rodents including mice, rats, and hamsters; and primates.

As used herein, "administering" or "delivering" a molecule or treatment to a cell (e.g., a molecule such as a linear or circular nucleic acid optionally in a delivery vehicle) includes contacting the molecule with the cell, e.g., by mixing, fusing, transducing, transfecting, microinjecting, electroporating, or shooting. For instance, for in vivo delivery, a molecule may be delivered via a device such as a catheter, cannula or needle.

The term "antibody," as used herein, refers to a full-length immunoglobulin molecule or an immunologically-active fragment of an immunoglobulin molecule such as the Fab or F(ab)2 fragment generated by, for example, cleavage of the antibody with an enzyme such as pepsin or co-expression of an antibody light chain and an antibody heavy chain in, for example, a mammalian cell, or ScFv. The antibody can also be an IgG, IgD, IgA, IgE or IgM antibody. Full-length immunoglobulin "light chains" (about 25 kD or 214 amino acids) are encoded by a variable region gene at the amino-terminus (about 110 amino acids) and a kappa or lambda constant region gene at the carboxy-terminus. Full-length immunoglobulin "heavy chains" (about 50 kD or 446 amino acids), are similarly encoded by a variable region gene (about 116 amino acids) and one of the other aforementioned constant region genes, e.g., gamma (encoding about 330 amino acids). Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. In each pair of the tetramer, the light and heavy chain variable regions are together responsible for binding to an antigen, and the constant regions are responsible for the antibody effector functions. In addition to naturally occurring antibodies, immunoglobulins may exist in a variety of other forms including, for example, Fv, ScFv, Fab, and F(ab')$_2$, as well as bifunctional hybrid antibodies (e.g., Lanzavecchia et al. (1987)) and in single chains (e.g., Huston et al. (1988) and Bird et al. (1988), which are incorporated herein by reference). (See, generally, Hood et al., "Immunology", Benjamin, N.Y., $2^{nd}$ ed. (1984), and Hunkapiller and Hood (1986), which are incorporated herein by reference). Thus, the term "antibody" includes antigen binding antibody fragments, as are known in the art, including Fab, Fab$_2$, single chain antibodies (scFv for example), chimeric antibodies, etc., either produced by the modification of whole antibodies or those synthesized do novo using recombinant DNA technologies.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., U.S. Department of Health and Human Services, (1983); which is incorporated herein by reference). The sequences of the framework regions of different light or heavy chains are relatively conserved within a species. As used herein, a "human framework region" is a framework region that is substantially identical (about 85% or more, usually 90 to 95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. One example of a chimeric antibody is one composed of the variable or antigen-binding domain from a mouse antibody and the constant or effector domain from a human antibody, although other mammalian species may be used.

As used herein, the term "humanized" immunoglobulin refers to an immunoglobulin having a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they are generally substantially identical to human immunoglobulin constant regions, i.e., at least about 85-90%, or about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. One says that the donor antibody has been "humanized", by the process of "humanization", because the resultant humanized antibody is expected to bind to the same antigen as the donor antibody that provides the CDR's.

Thus, humanized forms of non-human (e.g., murine) antibodies are chimeric immunoglobulins, immunoglobulin chains or fragments thereof (such as Fv, Fab, Fab', F(ab")2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody has substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will include at least a portion of an immunoglobulin constant region (Fc), typically that of a human immunoglobulin (Jones et al. (1988); Riechmann et al. (1988); and Presta (1992)).

It is understood that the humanized antibodies may have additional conservative amino acid substitutions which have substantially no effect on antigen binding or other immunoglobulin functions. By conservative substitutions are intended combinations such as gly, ala; val, ile, leu; asp, glu; asn, gln; ser, thr; lys, arg; and phe, tyr.

Humanized immunoglobulins, including humanized antibodies, have been constructed by means of genetic engineering. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522 (1986); Riechmann et al., *Nature*, 332:323 (1988): Verhoeyen et al., *Science*, 239:1534 (1988)), by substituting rodent CDRs or CDR sequences for the corresponding sequences of a human antibody. Accordingly, such "humanized" antibodies are chimeric antibodies that have substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies.

Human antibodies can also be produced using various techniques known in the art, including phage display libraries (Hoogenboom and Winter, *J. Mol. Biol.*, 227:381 (1991); Marks et al., *J. Mol. Biol.*, 2:581 (1991)). The techniques of Cole et al, and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol*, 147:86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in the following scientific publications: Marks et al., *Bio/Technology* 10:779 (1992); Lonberg et al., *Nature* 38:856 (1994); Morrison, *Nature,* 368:812 (1994) Fishwid et al., *Nature Biotechnology,* 14:845 (1996); Neuberger, *Nature Biotechnology,* 14:826 (1996); Lonberg and Huszar, *Intern. Rev. Immunol.,* 13:65 (1995). Most humanized immunoglobulins that have been previously described have a framework that is identical to the framework of a particular human immunoglobulin chain and three CDR's from a non-human donor immunoglobulin chain.

A framework may be one from a particular human immunoglobulin that is unusually homologous to the donor immunoglobulin to be humanized, or a consensus framework derived from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60-70%. By choosing one of the human heavy (respectively light) chain variable regions that is most homologous to the heavy (respectively light) chain variable region of the other immunoglobulin, fewer amino acids will be changed in going from the one immunoglobulin to the humanized immunoglobulin. The precise overall shape of a humanized antibody having the humanized immunoglobulin chain may more closely resemble the shape of the donor antibody, also reducing the chance of distorting the CDR's.

Typically, one of the 3-5 most homologous heavy chain variable region sequences in a representative collection of at least about 10 to 20 distinct human heavy chains is chosen as acceptor to provide the heavy chain framework, and similarly for the light chain. One of the 1 to 3 most homologous variable regions may be used. The selected acceptor immunoglobulin chain may have at least about 65% homology in the framework region to the donor immunoglobulin.

In many cases, it may be considered desirable to use light and heavy chains from the same human antibody as acceptor sequences, to be sure the humanized light and heavy chains will make favorable contacts with each other. Regardless of how the acceptor immunoglobulin is chosen, higher affinity may be achieved by selecting a small number or amino acids in the framework of the humanized immunoglobulin chain to be the same as the amino acids at those positions in the donor rather than in the acceptor.

Humanized antibodies generally have advantages over mouse or in some cases chimeric antibodies for use in human therapy: because the effector portion is human, it may interact better with the other parts of the human immune system (e.g., destroy the target cells more efficiently by complement-dependent cytotoxicity (CDC) or antibody-dependent cellular cytotoxicity (ADCC)); the human immune system should not recognize the framework or constant region of the humanized antibody as foreign, and therefore the antibody response against such an antibody should be less than against a totally foreign mouse antibody or a partially foreign chimeric antibody.

DNA segments having immunoglobulin sequences typically further include an expression control DNA sequence operably linked to the humanized immunoglobulin coding sequences, including naturally-associated or heterologous promoter regions. Generally, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, Cells of Immunoglobulin Synthesis, Academic Press, New York, (1979), which is incorporated herein by reference).

Other "substantially homologous" modified immunoglobins to the native sequences can be readily designed and manufactured utilizing various recombinant DNA techniques well known to those skied in the art. For example, the framework regions can vary at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gilman and Smith, *Gene,* 8:81 (1979) and Roberts et al., *Nature,* 2:731 (1987), both of which are incorporated herein by reference). Substantially homologous immunoglobulin sequences are those which exhibit at least about 85% homology, usually at least about 90%, or at least about 95% homology with a reference immunoglobulin protein.

Alternatively, polypeptide fragments comprising only a portion of the primary antibody structure may be produced, which fragments possess one or more immunoglobulin activities (e.g., antigen binding). These polypeptide fragments may be produced by proteolytic cleavage of intact antibodies by methods well known in the art, or by inserting stop codons at the desired locations in vectors known to those skilled in the art, using site-directed mutagenesis.

As used herein, the term "binds specifically" or "specifically binds," in reference to an antibody/antigen interaction, means that the antibody binds with a particular antigen (e.g., VEGF, EGFR or CXCL12) without substantially binding to other distinct antigens or to unrelated antigens. For example, in some embodiments, selected antibodies can bind with greater affinity to EGFRvIII than to EGFR. Thus, for example, the anti-EGFRvIII antibodies can have at least 50% or greater affinity, 60%, 70%, 80% or 90% greater affinity, to EGFRvIII than to EGFR. In other embodiments, for example, the anti-VEGF antibodies can have at least 50% or greater affinity, 60%, 70%, 80% or 90% greater affinity, to human VEGF than to murine VEGF.

Exemplary Cancer for Treatment with Gene Therapy Vectors of the Invention

Glioblastoma multiforme (GBM) is the most common and aggressive of primary human brain tumors (Park et al., 2010; Barker et al., 1998). Despite surgical resection, radiation, chemotherapy and a variety of other approaches, prognosis remains dismal with a median survival of about 14 months (VanMeir et al., 2010). No causative risk factors have been definitively identified (Deorah et al., 2006: Hess et al., 2004). The typical patient is >50 yr, males>females, and commonly Caucasian or Asian (Hess et al., 2004). Morphologically GBM is classified as astrocytoma (most common), oligodendroglioma and ependymoma (VanMeir et al., 2010). GBM often contains a complex mixture of cell types including glial, astrocyte and a small population of stem-like cells thought to contribute to the radioresistant phenotype leading to repopulation of GBM after radiation therapy (Altaner, 2008; Brennan et al., 2009; Christensen et al., 2011). GBM stem cells can differentiate into an endothelial-like morphology, contributing to its high vascularity (Wang et al., 2010). GBM stem cells share characteristics with neural stem cells, including the ability to form neurospheres, the capacity to differentiate into multiple lineages and close interaction with blood vessels with which they form a vascular niche (Altaner et al., 2008: Christensen et al., 2010; Gilbertsen et al., 2007). It has been proposed that neural stem cells are the cells of origin of GBM (Lottaz et al., 2010; Piccirillo et al., 2009). The cancer genome atlas (TCGA) has conducted a comprehensive analysis of GBM (Verhaak et al., 2010: Anonymous, 2008). The data demonstrates that GBM is characterized by genomic rearrangements and duplications, as well as point mutations affecting pathways of growth, apoptosis, invasion and vascularization (Shinojima et al., 2003; Brennan et al., 2009; Anonymous, 2008).

GBM is distinguished by prominent vascular proliferation, and rapid and invasive growth. Although studies of angiogenic growth and proliferation pathways of primary tumors has uncovered GBM sensitive targets, the systemic delivery of immunotherapies to block these targets in GBM clinical trials has not increased survival (Wang et al., 2010; Knizetova et al., 2008; Adamson et al., 2009; Jain et al., 2007: Pope et al., 2011: Von et al., 2011). The disadvantages of current GBM immunotherapeutic approaches include repeated administration, and delivery of high doses by the intravascular route, resulting in systemic distribution of the therapeutic monoclonal antibody (Von et al., 2011; Ebos and Pili, 2012). Although the targeted area for antibody therapy for CNS cancers is within the CNS, systemic delivery results in drug distribution to healthy non-targeted organs and there is limited diffusion of the monoclonal into the CNS tumor (Mancuso et al., 2006; Pitz et al., 2011; Agarwal et al., 2013).

Exemplary Targets and Delivery

Vascular endothelial growth factor, GBM are highly vascular and thus should be susceptible to angiogenesis inhibitors. Like many other tumors, GBM produce VEGF, a major inducer of angiogenesis (Knizetova et al., 2005). The classical form of VEGF (VEGF-A), functions through 3 receptors (VEGFR-1, VEGF-R2 and NRP-1) to induce cell growth (Ferrara, 2009). Bevacizumab (Avastin (Sofer-Podesta et al., 2009)) is an FDA approved humanized monoclonal that blocks VEGF-A (Homsi and Daud, 2007). It is widely used to treat metastatic colon and non-small cell lung cancer, and ocular vascular proliferative disorders (Kourlas and Abrams, 2007; Jenab-Wolcott and Giantonio 2009; Galfrascoli et al., 2010: Langer and Soria, 2010). Bevacizumab has been tried as a therapeutic for GBM with limited success (Peak and Levin, 2010; Pope et al., 2011). Unlike the application of bevacizumab for the treatment of macular degeneration where bevacizumab is injected directly into the eye (Kourlas and Abrams, 2007), the trials for GBM with bevacizumab to date use systemic delivery (Peak and Levin, 2010; Pope et al., 2011), and thus are limited by the blood brain barrier in achieving therapeutic levels in the CNS, even with transient blood brain barrier permeabilization (Boockvar et al., 2010; Lu et al., 2008).

Epidermal growth factor. EGF-related pathways are activated by several mechanisms in GMB. EGFR amplification and over-expression of EGFR is seen in about 40% of GBM and generally portends poor prognostic value (Huang et al., 2009; Lee et al., 2006). Activating mutations in EGFR, especially the EGFRvIII deletion which removes 5 exons, are also common and may exist with or without gene amplification (Boockvar et al., 2010; Lopez-Gines et al., 2010). For instance, EGFRvIII is constitutively activated and activates the AKT pathway which has a number of targets that enhance growth and inhibit cell death (Gan et al., 2009). The anti-EGFR monoclonal cetuximab has been tested in combination therapy for GBM and shown to be effective in small clinical studies (Pope et al., 2011). However, an antibody that specifically targets a mutated activated form of EGFR may be more selective. Anti-EGFRvIII Fab monoclonals have been produced and engineered for higher affinity (Beers et al., 2000: Gupta et al., 2010).

CXCL12. CXCL12 (SDF-1) is involved in GBM proliferation and invasion, exerting its activity through the CXCR4 receptor (Ehtesham et al., 2009; Ehtesham et al., 2006: Stevenson et al., 2008). Both ligand and receptor are expressed in human GBM allowing autocrine signaling (Barbero et al., 2003). Among the activities of CXCL12 is signaling through the REK1/2 and Akt pathways to activate proteases that are critical for matrix degradation, as a step in invasion (Wu at al., 2005). Monoclonal antibodies against CXRC4 have been shown to inhibit proliferation of GMB cell lines and block the effects of CXCL12 on GMB in vitro (Barbero et al., 2003). The sequence for an anti-CXCL12 monoclonal is available (Pogue et al. (2011), the disclosure of which is specifically incorporated herein).

VEGF, EGFRvIII, and CXCL12 were chosen as exemplary GBM sensitive targets because: (1) they represent 3 diverse aspects of GBM malignant growth: vascularization (VEGF), mutated constitutively activated growth factor (EGFRvIII), and extracellular cytokine growth factor activation of a proliferation/invasion pathway (CXCL12/CXCR4) (Zagzag et al., 2006; Ehtesham at al., 2009; Ehtesham et al., 2006: Stevenson et al., 2008): (2) for each, there is experimental evidence that a therapeutic monoclonal antibody would suppress the aberrant biology (Wang et al., 2010; Murakami et al., 1999; Wu et al., 2008); and (3) availability of the monoclonal antibody sequence to enable engineering of a therapeutic gene transfer vector.

In one clinical scenario, vector mediated therapy would be applied at the time of GBM surgical removal. As complete removal is not always feasible, in one embodiment, the therapy vector would be administered in the milieu of the excised tumor, and within 1 week, local neurons would likely begin expression of a therapeutic dosage of the monoclonal antibody thereby inhibiting GBM recurrence. The stability of neurons would ensure persistent expression of the monoclonal antibody, thereby preventing angiogenesis, EGFR activation, invasion and/or proliferation of the remaining tumor cells.

Gene Delivery Vectors

Gene delivery vectors include, for example, viral vectors, liposomes and other lipid-containing complexes, such as lipoplexes (DNA and cationic lipids), polyplexes, e.g., DNA complexed with cationic polymers such as polyethylene glycol, nanoparticles, e.g., magnetic inorganic nanoparticles that bind or are functionalized to bind DNA such as $FesO_4$ or $MnO_2$ nanoparticles, microparticles, e.g., formed of polylactide polygalactide reagents, nanotubes, e.g., silica nanotubes, and other macromolecular complexes capable of mediating delivery or a gene to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. A large variety of such vectors are known in the art and are generally available.

Gene delivery vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary viral gene delivery vectors are described below. Gene delivery vectors may be administered via any route including, but not limited to, intracranial, intrathecal, intramuscular, buccal, rectal, intravenous or intracoronary administration, and transfer to cells may be enhanced using electroporation and/or iontophoresis, and/or scaffolding such as extracellular matrix or hydrogels, e.g., a hydrogel patch. In one embodiment, a permeation enhancer is not employed to enhance indirect delivery to the CNS.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.,* 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion.

Adenoviral vectors have been shown to result in transient expression of therapeutic genes in vivo, peaking at 7 days and lasting approximately 4 weeks. The duration of transgene expression may be improved in systems utilizing neural specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., *Nat. Med.*, 8:864 (2002); Lynch et al., *Circ. Res.*, 80:197 (1997)).

Herpesvirus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature*, 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Exemplary Viral Vectors

AAV-mediated gene therapy has been used to treat CNS human disorders (Sondhi et al., 2007: Worgall et al., 2008; Souweidane et al., 2010). One focus has been on late infantile neuronal lipofuscinosis (LINCL, Batten disease), a fatal lysosomal storage disease of children (Jalanko and Braulke, 2009). Administration of an AAV serotype 2 vector coding for CLN2 (the mutated gene causing LINCL) to the CNS of experimental animals resulted in expression of tripeptidyl peptidase (TPP-I, the lysosomal protease coded by CLN2), primarily in neurons (Sondhi et al., 2005). Following toxicology studies, this therapy was assessed in 10 children, with CNS catheters inserted via 6 burr holes under general anesthesia. Follow-up over 18 months showed stabilization of disease progression in 6/10 children (Worgall et al., 2005). Assessment of 25 different AAV serotypes culminated in the choice of the AAVrh.10 serotype derived from rhesus macaque as a vector for CNS delivery (IND # BB13951) (Sondhi et al., 2007).

AAV was selected as an exemplary delivery vehicle and AAV-directed gene delivery was shown to overcome the challenges of repeated CNS administration, intravenous high dose administration, and distribution, thus potentially eliminating side-effects while maintaining a long term and effective dose directed at the site of the tumor (Sondhi et al., 2012). The AAVrh.10 vector described below mediates an excellent CNS expression profile with specificity for neurons (Sondhi et al., 2007; Souweidane et al., 2010).

As an example of the strategy to deliver monoclonal antibodies to the CNS, an AAVrh.10-based vector coding for bevacizumab, an anti-VEGF monoclonal, was prepared. When that vector was used to genetically modify cells, there was efficient assembly of an active monoclonal. The AAVrh.10BevMab construct binds to human VEGF165 but not the mouse VEGF164 homolog (Watanabe et al., 2008).

GMB cell lines or multiple low passage primary GMB generated representing diverse TCGA types and mutation profiles may be useful for in vitro and in vivo assessment of vectors other than AAVrh.10 (Table I).

TABLE I

Examples of Primary GBM Cell Lines

| Cell line | Pathological diagnosis | Cytogenetics (FISH)[2] | Genotype[3] | Transcriptional class[4] |
|---|---|---|---|---|
| GM09-01/46 | GBM WHO grade IV + oligo features | No EGFR/CEP7 amplification; no 1 p 19q del | +[MET, CDK6], −CDKN2A* | PN |
| GM09-02 | GBM WHO grade IV | >15 sig for EGFR, 2-4 sig for CEP7 in 92% | ++EGFR, +[MET, CDK6], −[PTPRD*, PTEN], −−CDKN2A | Class |
| GM09-03/61 | GBM WHO grade IV | 3-5 EGFR/CEP7 in 60% | ++EGFR*, +[MET, CDK6, MDM4], −[PTPRD, PTEN], −−CDKN2A | Class |
| GM09-04 | GBM WHO grade IV | 3 sig EGFR 55%; no 1p 19q del | ++EGFR, +[MET, CDK6], −−[CDKN2A, PTEN] | Class |
| GM10-01 | GBM WHO grade IV | No amplification | ++CDK6, +PDGFRA, −PTEN | Mes |

TABLE I-continued

Examples of Primary GBM Cell Lines

| Cell line | Pathological diagnosis | Cytogenetics (FISH)[2] | Genotype[3] | Transcriptional class[4] |
|---|---|---|---|---|
| GM10-02 | GBM WHO grade IV | >20 sig EGFR and 2-6 CEP7 in 97% | ++[CDK4, MDM2*], +[EGFR, MET, CDK6], −PTEN | Mes |
| GM10-03 | GBM WHO grade IV | Not available | ++EGFR*, +[MET, CDK6], −[PTPRD, PTEN], −−CDKN2A | Mes |
| GM10-04 | GBM WHO grade IV | Not available | ++[EGFR, MDM2], +[MET, PDGFRA, CDK6, MDM4], −PTEN | Mes |
| GM10-05 | GBM WHO grade IV | 3-4 sig EGFR/CEP7 in 41%; no MGMT methylation | ++PDGFRA, +[EGFR, MET, CDK6], −PTEN, −−CDKN2A | PN |
| GM10-06 | GBM WHO grade IV | 4-9 sig EGFR/CEP7 in 35%; neg for EGFRvIII | +[EGFR, MET, CDK6, MDM4], −PTEN | Mes |

[1]Cell lines derived from patient GBM available at low passage (<P3). Additional lines including GM11-01, GM11-02 and GM11-03 may also be employed.
[2]EGFR/CEP7 ratio (sig) is determined by fluorescent in situ hybridization as an index of EGFR amplification. Both the ratio as well as the fraction of cell shaving the amplification is scored.
[3]++ = amplification defined by log2 ratio >2; + = gain, defined by log2 ratio >0.25; − = loss, defined by log2 ratio <−0.25; −− = deletion, defined by log2 ratio <−1; * = evidence of rearrangement within the gene
[4]Mes = Mesenchymal; PN = Proneural; Class = Classic; Transcriptomal class assignment was based on the nearest centroid of reported classes in Verhaak et al. (2010). The samples were profiled on exon-specific micro arrays (Affymetrix) and compared to the TCGA (The Cancer Genome Atlas Network) data performed on the same platform.

Exemplary Antibodies and Other Ligands Useful in the Methods

In one embodiment, the gene therapy vector encodes an antibody that is selective for an antigen, e.g., the antibodies can have about 75% or greater affinity, or about 90% or greater affinity, to their selected antigen (e.g., VEGF, EGFR or CXCL12) than to other distinct or unrelated polypeptides.

An antibody directed against an antigen that is a target for central nervous system cancers, e.g., targets such as VEGF, EGFR or CXCL12, is generally a monoclonal antibody. A monoclonal antibody is a population of molecules having a common antigen binding site that binds specifically with a particular antigenic epitope. A monoclonal antibody can be obtained by selecting an antibody-producing cell from a mammal that has been immunized with, for instance, VEGF, EGFR or CXCL12, and fusing the antibody-producing cell, e.g., a B cell, with a myeloma to generate an antibody-producing hybridoma. A monoclonal antibody can also be obtained by screening a recombinant combinatorial library such as an antibody phage display library. See, for example, PHAGE DISPLAY—A LABORATORY MANUAL, Barbas, et al., eds. Cold Spring Harbor Laboratory Press, Cold Spring Harbor, N.Y., 2001; and Kontermann & Dübel, ANTIBODY ENGINEERING, Heidelberg: Springer-Verlag, Berlin, 2001. Techniques for preparing monoclonal antibody-secreting hybridoma cells are also described, for example, by Kohler and Milstein (1975) and Kozbor et al. (1983). A monoclonal antibody against VEGF, VEGFR, EGFR, CXCR4 or CXCL12 can also be prepared using other methods available in the art, such as, for example, expression from a recombinant DNA molecule, or screening of a recombinant combinatorial immunoglobulin library using a VEGF, VEGFR, EGFR, CXCR4 or CXCL12 polypeptide.

The antibodies can be evaluated for affinity to VEGF, VEGFR, EGFR, CXCR4 or CXCL12 using standard procedures including, for example, enzyme linked immunosorbent assay (ELISA) to determine antibody titer and protein A chromatography to obtain the antibody-containing an IgG fraction.

An antibody directed against VEGF, VEGFR, EGFR, CXCR4 or CXCL12 can be a murine, chimeric, humanized or fully human antibody. A murine antibody is an antibody derived entirely from a murine source, for example, an antibody derived from a murine hybridoma generated from the fusion of a mouse myeloma cell and a mouse B-lymphocyte cell. A chimeric antibody is an antibody that has variable regions derived from a non-human source, e.g., murine or primate, and constant regions derived from a human source. A humanized antibody has antigen-binding regions, e.g., complementarity-determining regions, derived from a mouse source, and the remaining variable regions and constant regions derived from a human source. A fully human antibody is antibody from human cells or derived from transgenic mice carrying human antibody genes.

Methods to generate chimeric and humanized monoclonal antibodies are also readily available in the art and include, for example, methods involving recombinant DNA technology. A chimeric antibody can be produced by expression from a nucleic acid that encodes a non-human variable region and a human constant region of an antibody molecule. See, for example, Morrison et al., (1984). A humanized antibody can be produced by expression from a nucleic acid that encodes non-human antigen-binding regions (complementarity-determining regions) and a human variable region (without antigen-binding regions) and human constant regions. See, for example, Jones et al., (1986); and Verhoeven et al. (1988). Completely human antibodies can be produced by immunizing engineered transgenic mice that express only human heavy and light chain genes. In this case, therapeutically useful monoclonal antibodies can then be obtained using conventional hybridoma technology. See, for example, Lonberg & Huszar (1995). Nucleic acids and techniques involved in design and production of antibodies are well known in the art. See, for example, Batra et al. (1994): Berdoz et al. (1995); Boulianne et al. (1984); Carson et al. (1986); Chiang et al. (1989); Cole et al. (1984); Jones et al. (1986); Larrick et al. (1989); Morrison (1992); Morrison et al. (1984): Orlandi et al. (1989); Sandhu (1992);

Gavilondo & Larrick (2000); Huston & George (2001); and Kipriyanov & Le Gall (2004).

Another method for generating antibodies involves a Selected Lymphocyte Antibody Method (SLAM). The SLAM technology permits the generation, isolation and manipulation of monoclonal antibodies without needing to generate a hybridoma. The methodology principally involves the growth of antibody forming cells, the physical selection of specifically selected antibody forming cells, the isolation of the genes encoding the antibody and the subsequent cloning and expression of those genes.

The nucleic acids encoding the antibodies can be mutated to optimize the affinity, selectivity, binding strength or other desirable property of an antibody. A mutant antibody refers to an amino acid sequence variant or an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. In one embodiment, mutant antibodies have at least 80%, at least 85%, at least 90%, or at least 95% amino acid sequence identity or similarity with the amino acid sequence of either the heavy or light chain variable domain of the reference antibody.

For example, antibodies can be directed against any VEGF, VEGFR, EGFR, CXCR4 or CXCL12 polypeptide, including any of the following polypeptide sequences. Nucleic acids encoding such antibodies can be readily obtained using procedures available in the art.

In one embodiment, antibodies are directed against a VEGF polypeptide. In some embodiments, the antibody is directed against or is specific for VEGF-A. The human VEGF-A gene is organized in eight exons. Alternative exon splicing results in the generation of four main VEGF isoforms, having 121, 165, 189, and 206 amino acids once the signal sequence has been removed (VEGF121, VEGF165, VEGF189, and VEGF206). VEGF165 is the predominant isoform. Numerous less frequent splice variants have been also reported, including VEGF145, VEGF183 VEGF162, and VEGF165b. VEGF121 fails to bind heparin and is a freely diffusible protein; VEGF165 is secreted but a significant fraction remains bound to the cell surface and the extracellular matrix, by virtue of its heparin-binding properties. The highly basic VEGF189 is almost completely bound to the extracellular matrix. There is some evidence indicating that VEGF165 is the most physiologically relevant isoform.

One example of a VEGF sequence is the following, which is further described by the National Center for Biotechnology Information (see website at ncbi.nlm.nih.gov), which provides this sequence as accession number NP 571483.1 (GI:18859545) (SEQ ID NO:1).

```
  1  MNLVVYLIQL FLAALLHLSA VKAAHIPKEG GKSKNDVIPF
 41  MDVYKKSACK TRELLVDIIQ EYPDEIEKTY IPSCVVLMRC
 61  AGCCNDEALE CVPTETRNVT MEVLRVKQRV SQHNFQLSFT
121  EHTKCECRPK AEVKAKKENH CEPCSERRKR LYVQDPLTCK
161  CSCKFTQMQC KSRQLELNER TCRCEKPR
```

One example of a sequence for a human VEGF is available from the National Center for Biotechnology Information (see website at ncbi.nlm.nih.gov) as accession number P00533.2 (GI:2811086), provided below as SEQ ID NO:2.

```
   1  MRPSGTAGAA LLALLAALCP ASRALEEKKV CQGTSNKLTQ
  41  LGTFEDHFLS LQRMFNNCEV VLGNLEITYV QRNYDLSFLK
  81  TIQEVAGYVL IALNTVERIP LENLQIIRGN MYYENSYALA
 121  VLSNYDANKT GLKELPMRNL QEILHGAVRF SNNPALCNVE
 161  SIQWRDIVSS DFLSNMSMDF QNHLGSCQKC DPSCPNGSCW
 201  GAGEENCQKL TKIICAQQCS GRCRGKSPSD CCHNQCAAGC
 241  TGPRESDCLV CRKFRDEATC KDTCPPLMLY NPTTYQMDVN
 281  PEGKYSFGAT CVKKCPRNYV VTDHGSCVRA CGADSYEMEE
 321  DGVRKCKKCE GPCRKVCNGI GIGEFKDSLS INATNIKHFK
 361  NCTSISGDLH ILPVAFRGDS FTHTPPLDPQ ELDILKTVKE
 401  ITGFLLIQAW PENRTDLHAF ENLEIIRGRT KQHGQFSLAV
 441  VSLNITSLGL RSLKEISDGD VIISGNKNLC YANTINWKKL
 481  FGTSGQKTKI ISNRGENSCK ATGQVCHALC SPEGCWGPEP
 521  RDCVSCRNVS RGRECVDKCN LLEGEPREFV ENSECIQCHP
 561  ECLPQAMNIT CTGRGPDNCI QCAHYIDGPH CVKTCPAGVM
 601  GENNTLVWKY ADAGHVCHLC HPNCTYGCTG PGLEGCPTNG
 641  PKIPSIATGM VGALLLLLVV ALGIGLFMRR RHIVRKRTLR
 681  RLLQERELVE PLTPSGEAPN QALLRILKET EFKKIKVLGS
 721  GAFGTVYKGL WIPEGEKVKI PVAIKELREA TSPKANKEIL
 761  DEAYVMASVD NPHVCRLLGI CLTSTVQLIT QLMPFGCLLD
 801  YVREHKDNIG SQYLLNWCVQ IAKGMNYLED RRLVHRDLAA
 841  RNVLVKTPQH VKITDFGLAK LLGAEEKEYH AEGGKVPIKW
 881  MALESILHRI YTHQSDVWSY GVTVWELMTF GSKPYDGIPA
 921  SEISSILEKG ERLPQPPICT IDVYMIMVKC WMIDADSRPK
 961  FRELIIEFSK MARDPQRYLV IQGDERMHLP SPTDSNFYRA
1001  LMDEEDMDDV VDADEYLIPQ QGFFSSPSTS RTPLLSSLSA
1041  TSNNSTVACI DRNGLQSCPI KEDSFLQRYS SDPTGALTED
1081  SIDDIFLPVP EYINQSVPKR PAGSVQNPVY HNQPLNPAPS
1121  RDPHYQDPHS TAVGNPEYLN TVQPTCVNST FDSPAHWAQK
1161  GSHQISLDNP DYQQDFFPKE AKPNGIFKGS TAENAEYLRV
1201  APQSSEFIGA
```

In one embodiment, a gene therapy vector for use in the invention encodes an antibody that specifically binds to SEQ ID NO:1 or SEQ ID NO:2, or a polypeptide with at least 80%, 85%, 90%, 92%, 95%, 98% or 99% amino acid sequence identity thereto.

In one embodiment, antibodies are directed against a EGFR polypeptide, e.g., a variant EGFR such as EGFRvIII. One example of a variant EGFR sequence is the following:

```
                                    (SEQ ID NO: 15)
MRPSGTAGAALLALLAALCPASRALEEKKGNYVVTDHGSCVRACGADSYEM

EEDGVRKCKKCEGPCRKVCNGIGIGEFKDSLSINATNIKHFKNCTSISGDL

HILPVAFRGDSFTHTPPLDPQELDILKTVKEITGFLLIQAWPENRTDLHAF

ENLEIIRGRTKQHGQFSLAVVSLNITSLGLRSLKEISDGDVIISGNKNLCY

ANTINWKKLFGTSGQKTKIISNRGENSCKATGQVCHALCSPEGCWGPEPRD

CVS.
```

In one embodiment, a gene therapy vector for use in the invention encodes an antibody that specifically binds to SEQ ID NO:15, or a polypeptide with at least 80%, 85%, 90%, 92%, 95%, 98% or 99% amino acid sequence identity thereto.

In one embodiment, a gene therapy vector for use in the invention encodes an antibody that binds to SEQ ID NO:3 or a polypeptide with at least 80%, 85%, 90%, 92%, 95%, 98% or 99% amino acid sequence identity thereto.

Bevacizumab is a recombinant humanized monoclonal IgG1 antibody that binds to and inhibits the biologic activity of human vascular endothelial growth factor (VEGF). Bevacizumab contains human framework regions and the complementarity-determining regions of a murine antibody that binds to VEGF. Bevacizumab has been produced in a Chinese Hamster Ovary mammalian cell expression system in a nutrient medium containing the antibiotic gentamicin and has a molecular weight of approximately 149 kilodaltons.

Bevacizumab Amino acid sequences are as follows:

```
>1bj1_H|Fab-12, F(ab)-12, 12-IgG1, rhuMAb-VEGF|||VH-CH1 (VH(1-123) +
CH1(124-215))|||||||231||||MW 24867.8|MW 24867.8|
                                                          SEQ ID NO: 4
EVQLVESGGGLVQPGGSLRLSCAASGYTFTNYGMNWVRQAPGKGLEWVGWINTYTGEPTYAADFKRR

FTFSLDTSKSTAYLQMNSLRAEDTAVYYCAKYPHYYGSSHWYFDVWGQGTLVTVSSASTKGPSVFPLAP

SSKSTSGGTAALGCLVKDYFPEPVTVSWNSGALTSGVHTFPAVLQSSGLYSLSSVVTVPSSSLGTQTYIC

NVNHKPSNTKVDKKVEPKSCDKTHT

>1bj1_L|Fab-12, F(ab)-12, 12-IgG1, rhuMAb-VEGF|||L-KAPPA (V-KAPPA(1-107) +
C-KAPPA(108-213))|||||||214||||MW 23451.0|MW 23451.0|
                                                          SEQ ID NO: 5
DIQMTQSPSSLSASVGDRVTITCSASQDISNYLNWYQQKPGKAPKVLIYFTSSLHSGVPSRFSGSGSGTD

FTLTISSLQPEDFATYYCQQYSTVPWTFGQGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVTKSFN

RGEC

>1bj1_J|Fab-12, F(ab)-12, 12-IgG1, rhuMAb-VEGF|||L-KAPPA (V-KAPPA(1-107) +
C-KAPPA(108-213))|||||||214||||MW 23451.0|MW 23451.0|
                                                          SEQ ID NO: 6
DIQMTQSPSSLSASVGDRVTITCSASQDISNYLNWYQQKPGKAPKVLIYFTSSLHSGVPSRFSGSGSGTD

FTLTISSLQPEDFATYYCQQYSTVPWTFGQGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVIKSFN

RGEC

>1bj1_K|Fab-12, F(ab)-12, 12-IgG1, rhuMAb-VEGF|||VH-CH1 (VH(1-123) +
CH1(124-215)|||||||)231||||MW 24867.8|MW 24867.8|
                                                          SEQ ID NO: 7
EVQLVESGGGLVQPGGSLRLSCAASGYTFTNYGMMIWRQAPGKGLEVVVGWNTYTGEPTYAADFKRR

FIFSLDISKSTAYLQUINSLRAEDTAVYYCAKYPHYYGSSHWYEDVVVGQGTLVTVSSASTKGPSVFPLAR

SSKSTSGGTAALGCLVKDYFPEPVTVSWNSGALTSGVHIFPAVLQSSGLYSLSSVVIVPSSSLGIQTY1C

NVNHKPSNTKVDKKVEPKSCDKTHT
```

One example of a sequence for a human CXCL12 (also called SDF1) is available from the National Center for Biotechnology Information (see website at ncbi.nlm.nih.gov) as accession number P48061.1 (GI:1352728), provided below as SEQ ID NO:3.

```
  1   MNAKVVVVLV LVLTALCLSD GKPVSLSYRC PCRFFESHVA

41   RANVKHLKIL NTPNCALQIV ARLKNNNRQV CIDPKLKWIQ

81   EYLEKALNKR FKM
```

In one embodiment, a gene therapy vector for use in the invention encodes an antibody having any one of SEQ ID Nos. 4-7 or a polypeptide with at least 80%, 85%, 90%, 92%, 95%, 98% or 99% amino acid sequence identity thereto.

Other anti-VEGF antibodies or VEGFR ligands useful in the methods include but are not limited to B20-4; G-6; ramucirumab; IMC-18F1; VEGF-Trap, a fusion protein (aflibercept; Holash et al., *Proc. Natl. Acad. Sci. USA.* 2:11393 (2002)); sFLT, and a soluble VEGFR receptor (a splice variant of VEGFR-1 (Khalil et al., *PloS ONE.*, 2:e2766 (2008)), as well as polypeptides with at least 80%, 85%, 90%, 92%, 95%, 98% or 99% amino acid sequence identity thereto.

Cetuximab is epidermal growth factor receptor (EGFR) binding FAB. Cetuximab is composed of the Fv (variable; antigen-binding) regions of the 225 murine EGFR monoclonal antibody specific for the N-terminal portion of human EGFR with human IgG1 heavy and kappa light chain constant (framework) regions.

>Anti-EGFR heavy chain 1
(SEQ ID NO: 8)
QVQLKQSGPGLVQPSQSLSITCTVSGFSLINYGVHWVRQSPGKGLEWLGVI

WSGGNTDYNTPFTSRLSINKDNSKSQVFFKMNSLQSNDTAIYYCARALTYY

DYEFAYWGQGTLVIVSAASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKRVEPKSPKSCDKTHTCPPCPAPELLGGPSVFLFPPKPKDT

LMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK

>Anti-EGFR light chain 1
(SEQ ID NO: 9)
DILLTQSPVILSVSPGERVSFSCRASQSIGTNIHWYQQRTNGSPRLLIKYA

SESISGIPSRFSGSGSGTDFTLSINSVESEDIADYYCQQNNNWPTTFGAGT

KLELKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGA

>Anti-EGFR heavy chain 2
(SEQ ID NO: 10)
QVQLKQSGPGLVQPSQSLSITCTVSGFSLTNYGVHWVRQSPGKGLEWLGVI

WSGGNIDYNTPFTSRLSINKDNSKSQVFFKMNSLQSNDTAIYYCARALTYY

DYEFAYWGQGTLVTVSAASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKRVEPKSPKSCDKTHTCPPCPAPELLGGPSVFLFPPKPKDT

LMISRTPEVTCVVVDVSHEDFEVKFNWYVDGVEVHNAKTKPREEQYNSTYR

VVSVLTVLHQDWLNGKEYKCKVSNKALPAPIEKTISKAKGQPREPQVYILP

PSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK

>Anti-EGFR light chain 2
(SEQ ID NO: 11)
DILLTQSPVILSVSPGERVSFSCRASQSIGTNIHWYQQRTNGSPRLLIKYA

SESISGIPSRFSGSGSGTDFTLSINSVESEDIADYYCQQNNNWPTTFGAGT

KLELKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGA

See also SEQ ID NO:1 in U.S. Pub PG 201210115739, the disclosure of which is incorporated by reference herein.

In one embodiment, a gene therapy vector for use in the invention encodes an antibody having any one of SEQ ID Nos. 8-11 or a polypeptide with at least 80%, 85%, 90%, 92%, 95%, 98% or 99% amino acid sequence identity thereto.

Other anti-EGFR antibodies or ligands useful in the methods include but are not limited to panitumumab; zalutumumab; GA201; R67160: ABX-EGF (Schwartz et al. (2002); EMD72000; MAb ICR62; h-R3; MDX-447; MDX-H210; the anti-EFGR vIII antibody in Gupta et al., (2011) and the parent thereof: mAb 806 and 2C4 (Luwor et al., Cancer Res., 61:5355 (2001); Agus et al., J. Clin. Oncol., 25:675 (2007), and antibodies in immunoconjugates Y10, Ua30:2, and Mab806, or a polypeptide with at least 80%, 85%, 90%, 92%, 95%, 98% or 99% amino acid sequence identity thereto.

Other anti-CXCL12 antibodies or ligands useful in the methods include but are not limited to nanobodies (Blanchetot et al. (2013)); 30b8 (Zhong et al. (2013)); cTCE-9908 (see U.S. Pat. No. 6,946,445): POL6326; TG-0054; and anti-CXCR4 antibodies including those in Vaday et al. (2004) and Bertolini et al. 2002), and BMS-936564/MDX-1338 (Kuhne et al., (2013)), or a polypeptide with at least 80%, 85%, 90%, 92%, 95%, 98% or 99% amino acid sequence identity thereto.

In addition, some GBM express Her-2/neu (EGFR-2, ErbB2) and so vectors expressing anti-Her-2/neu antibodies, e.g., trastuzumab (Herceptin); CB11 (MA1-34495); HER-2; SP4; 4B5, or EP4, or a polypeptide with at least 80%, 85%, 90%, 92%, 95%, 98% or 99% amino acid sequence identity thereto, or other ligands of EGFR-2, may be employed in the methods of the invention.

Routes of Administration, Dosages and Dosage Forms

Administration of the gene delivery vectors in accordance with the present invention may be continuous or intermittent, depending, for example, upon the recipient's physiological condition, and other factors known to skilled practitioners. The administration of the gene delivery vector(s) may be essentially continuous over a preselected period of time or may be in a series of spaced doses. Both local administration, e.g., intracranial, intranasal or intrathecal, and systemic administration, e.g., using viruses that cross the blood-brain barrier, are contemplated.

One or more suitable unit dosage forms comprising the gene delivery vector(s), which may optionally be formulated for sustained release, can be administered by a variety of mutes including intracranial, intrathecal, or intranasal, or other means to deliver to the CNS, or oral, or parenteral, including by rectal, buccal, vaginal and sublingual, transdermal, subcutaneous, intravenous, intramuscular, intraperitoneal, intrathoracic, or intrapulmonary routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

The amount of gene delivery vector(s) administered to achieve a particular outcome will vary depending on various factors including, but not limited to, the genes and promoters chosen, the condition, patient specific parameters, e.g., height, weight and age, and whether prevention or treatment, is to be achieved.

Vectors of the invention may conveniently be provided in the form of formulations suitable for administration, e.g., into the brain. A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. By "pharmaceutically acceptable" it is meant a carrier, diluent, excipient, and/or salt that is compatible with the other ingredients of the formulation, and not deleterious to the recipient thereof.

Vectors of the present invention may be formulated in solution at neutral pH, for example, about 40 pH 6.5 to about pH 8.5, or from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, or from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is useful for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about 107 viral particles, e.g., about $10^9$ viral particles, or about $10^{11}$ viral particles. The number of viral particles added may be up to $10^{14}$. As noted, the exact dose to be administered is determined by the attending clinician, but may be in 1 mL phosphate buffered saline. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

In one embodiment, administration may be by intracranial injection using an appropriate catheter or needle. A variety of catheters may be used to achieve delivery, as is known in the art. For example, a variety of general purpose catheters, as well as modified catheters, suitable for use in the present invention are available from commercial suppliers. Also, where delivery is achieved by injection directly into a specific region or the brain, a number of approaches can be used to introduce a catheter into that region, as is known in the art.

By way of illustration, liposomes and other lipid-containing gene delivery complexes can be used to deliver one or more transgenes. The principles of the preparation and use of such complexes for gene delivery have been described in the art (see, e.g., Ledley, (1995); Miller et al., (1995); Chonn et al., (1995); Schofield et al., (1995); Brigham et al., (1993)).

Pharmaceutical formulations containing the gene delivery vectors can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions appropriate for parenteral administration, for instance, by intramuscular, subcutaneous or intravenous routes.

The pharmaceutical formulations of the vectors can also take the form or an aqueous or anhydrous solution, e.g., a lyophilized formulation, or dispersion, or alternatively the form of an emulsion or suspension.

In one embodiment, the vectors may be formulated for administration, e.g., by injection, for example, bolus injection or continuous infusion via a catheter, and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector may be administered via nose drops, a liquid spray, such as via a plastic bottle atomizer or metered-dose inhaler. Typical of atomizers are the Mistometer (Wintrop) and the Medihaler (Riker).

The local delivery of the vectors can also be by a variety of techniques which administer the vector at or near the site of disease, e.g., using a catheter or needle Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

The formulations and compositions described herein may also contain other ingredients such as antimicrobial agents or preservatives.

Compositions Useful in the Methods

The invention also relates to compositions containing a nucleic acid that encodes an antibody directed against VEGF, VEGFR, EGFR, CXCR4, or CXCL12, encodes an antagonistic ligand of VEGFR, EGFR or CXCR4, or a combination thereof. The compositions can include an expression cassette or vector that encodes one or more of such nucleic acids. The compositions can also contain a carrier, for example, a pharmaceutically acceptable carrier.

In some embodiments, the therapeutic agents of the invention (e.g., a nucleic acid that encodes an antibody directed against VEGF, VEGFR, EGFR, CXCR4, or CXCL12, encodes an antagonistic ligand of VEGFR, EGFR or CXCR4, or a combination thereof, or a vector that includes such a nucleic acid), are administered in a "therapeutically effective amount." Such a therapeutically effective amount is an amount sufficient to obtain the desired physiological effect, e.g., treatment of a condition, disorder, disease and the like or reduction in symptoms of the condition, disorder, disease and the like. For example, the therapeutic agents can be administered to treat a condition, disorder, or disease such as cancer, especially malignant cancer of the central nervous system.

To achieve the desired effect(s), the nucleic acid that encodes an antibody directed against VEGF, VEGFR, EGFR, CXCR4, or CXCL12, encodes an antagonistic ligand of VEGFR, EGFR or CXCR4, or a combination thereof, or a vector that includes such a nucleic acid, may be administered as single or divided dosages. For example, when a viral expression vector is employed, about $10^8$ to about $10^{60}$ gc of viral vector can be administered as nucleic acid or as a packaged virion. In some embodiments, about $10^9$ to about $10^{15}$ copies of viral vector, e.g., per 0.5 to 10 mL, can be administered as nucleic acid or as a packaged virion. Alternatively, the nucleic acids or vectors, can be administered in dosages of at least about 0.0001 mg/kg to about 1 mg/kg, of at least about 0.001 mg/kg to about 0.5 mg/kg, at least about 0.01 mg/kg to about 0.25 mg/kg or at least about 0.01 mg/kg to about 0.25 mg/kg of body weight, although other dosages may provide beneficial results. The amount administered will vary depending on various factors including, but not limited to, the nucleic acid or vector chosen for administration, the disease, the weight, the physical condition, the health, and/or the age of the mammal. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents and compositions of the invention may be essentially continuous over a preselected period of time or may be in a series of spaced doses. Both local and systemic administration is contemplated.

To prepare the composition, nucleic acids or vectors, and other agents are synthesized or otherwise obtained, purified as necessary or desired and then lyophilized and stabilized. These agents can then be adjusted to the appropriate concentration, and optionally combined with other agents. The absolute weight of a given nucleic acid or vector included in a unit dose can vary widely.

The compositions of the invention may be prepared in many forms that include aqueous solutions, suspensions, tablets, hard or soft gelatin capsules, and liposomes and other slow-release formulations, such as shaped polymeric gels. In some embodiments, administration of nucleic acids or vectors involves parenteral or local administration of the nucleic acids or vectors in an aqueous solution or sustained release vehicle.

The invention will be described by the following non-limiting example.

Example

Studies of human GBM have identified several biologic processes linked to the GBM malignant state. CNS administration of gene transfer vectors may be used to genetically modify neurons to continuously express therapeutic monoclonal antibodies or other protein molecules that will suppress the aberrant biologic processes fundamental to GBM malignancy. This approach circumvents the challenge of the blood-brain barrier, providing local production and thus high local levels of the therapeutic molecules in the CNS. Such a strategy was employed to bypass those barriers using CNS administration of adeno-associated virus (AAV) gene transfer vectors to deliver the genetic sequences for monoclonal antibodies, thereby modifying normal CNS cells to chronically deliver therapeutic monoclonal antibodies in the local milieu, which in turn suppress the growth of human GBM in the CNS. Because neurons do not turn over, the expression of the monoclonal is persistent, an important feature in treating GBM, where it is not feasible to surgically remove all of the tumor (Park et al., 2010; Barker et al., 1995).

Based on the enhancement of tumor growth by GBM production or vascular endothelial growth factor (VEGF), a tumor-produced, secreted angiogenic mediator required for generation of blood vessels for GBM (Wang et al., 2010; Zagzag et al., 2008), a monoclonal directed against VEGF was tested for anti-tumor angiogenic activity. Since approximately 40% of human GBM express epidermal growth factor receptor (EGFR) vIII, a mutated, constitutively activated form of EGFR that stimulates tumor growth (Ongaki et al. 2007; Shinojima et al., 2005), an anti-EGFRvIII monoclonal antibody that suppresses EGFRvIII function was tested for anti-tumor growth activity. GBM overexpress CXCL12 (stromal derived factor 1, SDF1, the ligand for CXCR4), a GBM proliferation-, dissemination- and invasion-promoting pathway (Ehtesham et al., 2009; Ehtesham et al., 2006; Stevenson at al., 2008). Genetic delivery of an anti-CXCL12 monoclonal antibody that suppresses CXCL12 function by sequestering CXCL12, a GBM proliferation/invasion-promoting pathway function, was also evaluated.

Methods

Recombinant AAVrh.10 Vectors

The AAVrh.10BevMab vector is based on the non-human primate-derived rh.10 capsid pseudotyped with AAV2 inverted terminal repeats surrounding the anti-VEGF antibody expression cassette. The expression cassette has the cytomegalovirus (CMV) enhancer-chicken-□-actin promoter, the bevacizumab monoclonal heavy chain coding sequence, a 4-amino-acid furin cleavage site and the 24-amino-acid self-cleaving 2A peptide, the bevacizumab light chain coding sequence, and the rabbit β-globin polyadenylation signal (Fang et al., 2005; Watanabe et al., 2010; Mao et al., 2011). The cDNA sequence of the VEGF antibody heavy chain (IgG1) and light chain (κ chain) were as previously described in Watanabe et al. (2008). The negative control vector AAVrh.10anticoc.Mab (referred to as "AAVcontrol") encodes an irrelevant antibody directed against cocaine (Rosenberg et al., 2012).

AAVrh.10BevMab was produced by Polyfect-mediated (Qiagen) cotransfection into human embryonic kidney 293 cells (HEK 293; American Type Culture Collection) of two plasmids, pAAVαVEGF (500 μg), and pPAKMArh.10 (1.0 mg): (1) pAAVαVEGF is an expression plasmid containing (5' to 3') the AAV2 5'-inverted terminal repeat including packaging signal (ψ), the expression cassette of the humanized anti-VEGF monoclonal antibody bevacizumab and the AAV2 3'-inverted terminal repeat; and (2) pPAKMArh.10 is a helper and packaging plasmid that provides the AAV Rep proteins derived from AAV2 needed for vector replication, the AAVrh.10 viral structural (Cap) proteins VP1, 2 and 3, which define the serotype of the produced AAV vector and Ad helper plasmid that provides Ad helper functions of E2, E4 and $V_A$ RNA. At 72 hours after transfection, the cells were harvested; a crude viral lysate was prepared by four cycles of freeze/thaw and then clarified by centrifugation. AAVrh.10BevMab was purified by iodixanol gradient and QHP anion exchange chromatography, concentrated with an Amicon Ultra-15 100K centrifugal filter device (Millipore) and stored in PBS, pH 7.4, −80° C. The control vector was produced by the same method with pAAVanticoc, a plasmid coding for a monoclonal antibody against cocaine, substituted for pAAVαVEGF. Vector genome titers were determined by quantitative TaqMan quantitative PCR using a cytomegalovirus promoter-specific primer-probe set (Applied Biosystems).

To verify AAVrh.10BevMab-directed expression of bevacizumab, HEK 293 cells were infected with AAVrh.10BevMab at $2\times10^5$ genome copies (gc) per cell (or mock infected), supernatant was harvested 72 hours later and immunoglobulin was purified with protein G sepharose. Bevacizumab expression was evaluated by coomassie blue stain SDS-PAGE and Western analysis with a sheep anti-human IgG heavy chain and light chain secondary antibody (Sigma) and an enhanced chemiluminescence reagent (Amersham).

Murine Experimental Animal Model of GBM Delivery

U87MG (American Type Culture Collection, Manassas, VA) glioblastoma cells were cultured in Eagle's Minimum Essential Medium in fetal bovine serum (10%). Low passage primary human glioblastoma cell (0709) were derived from human patients and cultured in DMEM/F12 with epidermal growth factor (EGF) and basic fibroblast growth factor (bFGF) each at 20 ng/mL on 10 cm plates (BD Biosciences, San Jose, CA) that have been coated with poly-L-omithine (1:1000 of 15 mg/m), laminin (1:250 of 1 mg/mL, R&D Systems. Minneapolis, MN) and fibronectin (1:500 of 1 mg/mL, BD Biosciences).

The most likely clinical use of AAVrh.10BevMab for treatment of glioblastoma would be to remove as much tumor as possible, and after tumor removal (at the time of surgery), to administer the AAVrh.10BevMab vector in the local CNS region. Based on the knowledge that the AAVrh.10BevMab would be expressed within 1 week, the local expression of bevacizumab would likely contribute to suppression of growth of residual tumor cells post-surgery. Thus, AAVrh.10BevMab therapy or controls (PBS or an AAVrh.10 vector coding for an irrelevant antibody) were administered to the CNS simultaneously with the tumor cells or 6 days after implantation of the tumor cells.

Female NOD/SCID immunodeficient mice, 6 to 8 week old (Jackson, Bar Harbor, ME) were housed under pathogen-free conditions. At 7 to 10 weeks of age the mice were treated with AAVrh.10BevMab or AAVcontrol at $10^{11}$ genome copies (gc) by direct CNS administration in 2 to 5 µL. CNS administration to the right hemisphere of the tumor cells and the vector were administered stereotaxicaly in the lower striatum (A/P+1.0 mm, M/L±1.0 mm, D/V −3.0 mm), at a rate of 0.5 µL/min using a 10 µL syringe (Hamilton. Reno, NV) with a 26 g needle. The needle was left in position for 2 minutes before and 2 minutes following administration, at which point it was withdrawn slightly (1 mm) and left for 1 minute, and then fully withdrawn over the course of an additional minute.

For the concurrent administration of U87MG tumor cells and therapy, $10^5$ cells were administered in a total volume of 2 µL together with $10^{11}$ gc AAVrh.10BevMab or control (AAVrh.10 vector coding for an irrelevant antibody or PBS) in a volume of 3 µL (total volume 5 µL). For the U87MG cells treated 6 days after tumor administration, $10^5$ U87MG cells were administered in a volume of 2 µL, followed 6 days later by $10^{11}$ gc AAVrh.10BevMab in a volume of 2 µL. For the 0709 low passage primary cells, $10^5$ cells were administered in a total volume of 3 µL together with $10^{11}$ gc AAVrh.10BevMab or control (AAVrh.10 vector coding for an irrelevant antibody or PBS) in a volume of 3 µL (total volume 6 µL). All animal studies were conducted under protocols reviewed and approved by the Weill Cornel Institutional Animal Care and Use Committee.

Quantification of Bevacizumab

Samples of brain tissue were collected after perfusion with cold phosphate buffered saline (PBS, pH 7.4). Coronal sections divided the 2 hemispheres into 4 segments (equidistance anterior to posterior). Blood was obtained from the tail vein, allowed to clot for 1 hour, 23° C., followed by 30 minutes, at 4° C., and then spun in microcentrifuge at 10,000 g for 20 minutes to collect serum. The levels of anti-VEGF antibody were determined by ELISA. Wells of flat bottomed 96-well EIA/RIA plates (Corning, Corning, NY) were coated with 100 µL of 0.2 mg/mL VEGF165 (R&D Systems), in carbonate-buffer at pH 9.0 overnight at 4° C., and then washed with 0.05% Tween 20 in PBS (PBS-Tween) and blocked with 5% dry milk in PBS for 30 minutes, 23° C. Serial dilutions of sera were added to the 96-wells and incubated for 90 minutes, 23° C. The plates were washed 4 times with PBS-Tween and 100 µL of 1:2000 diluted goat anti-human IgG conjugated to horseradish peroxidase (Sigma-Aldrich, St. Louis, MO) in 1% dry milk in PBS, incubated for 90 minutes, 23° C. After 4 wash steps, peroxidase substrate (100 µl/well; Bio-Rad, Hercules, CA) was added to each well, incubated for 15 minutes at 23° C., and the reaction was stopped with addition of 2% oxalic acid (100 µL/well. Absorbance was measured at 415 nm. Bevacizumab antibody titers were calculated by interpolation of the log(OD)-log(dilution) with a cutoff value equal to twice the absorbance of background and converted to µg/ml based on standard curve with the VEGF antibody. Total protein levels were quantified by the bicinchoninic acid assay (Pierce Biotechnology, Rockford, IL).

Immunohistochemical Analysis

AAVrh.10BevMab transduction of the mouse brain cells was assessed by immunohistochemical staining for bevacizumab. Mouse brains were perfused with 4% paraformaldehyde formulated in PBS, then stored in 4% paraformaldehyde/PBS at 4° C., equilibrated in 15% sucrose at 4° C. for 24 to 48 hours, followed by an equilibration in 30% sucrose at 4° C. for 48 to 72 hours. Serial 10 to 100 µm thick frozen coronal sections were produced with a microtome (Histoserv Inc, Germantown, MD). Immunohistochemical detection of bevacizumab was detected with anti-human kappa IgG antibody (1:100; overnight at 4° C.; Sigma). Secondary antibodies conjugated to the fluorophores Alexa 488, Alex 555 or Alexa 647 (Invitrogen, Carlsbad, CA) used to visualize the staining pattern. Fluorescence imaging was performed with an Olympus Fluoview confocal microscope (Olympus America, Center Valley, PA). For quantification of blood vessel density, frozen sections were stained with endothelial cell marker CD31 and counterstained with anti-human specific antigen and DAPI. Quantification of tumor blood vessel density was calculated separately in tumors and normal area of control-treated mice compared to AAVrh.10BevMab-treated mice.

Magnetic Resonance Imaging (MRI) Quantification

MRI was performed on a 7.0 Tesla 70/30 Bruker Small Animal MRI scanner (Bruker Biospin, Bilerica, MA) equipped with an additional small animal imaging gradient set (45 G/cm). Animals were imaged under isoflurane anesthesia (2% to initiate anesthesia, 1% for maintenance). A warming bed was used to maintain a constant body temperature and respiration was also monitored throughout the imaging procedure.

High-resolution imaging sequences were acquired prior to and following tail vein administration of the MRI contrast agent, gadopentetate dimeglumine (Gd-DTPA; Bertex Laboratories; Wayne, NJ; 8 nmol/mouse in 40 µL volume). A T1-Weighted 2D FLASH sequence was used to visualize contrast enhancement with a repetition time of 357 ms and an echo time of 3.8 ms. T2-Weighted Turbo RARE sequences were also acquired with repetition and echo times of 2300 ms/48 ms respectively to detect edema. A 20 mm field of view and 256×258 matrix produced an image resolution of 78 µm×78 µm×500 µm with 20 matching axial slices.

Tumor burden was assessed for the U87GM line T1 (Gd-DTPA enhanced) and T2 weighted sequences using IDL 8.1 custom coded algorithms (Exelis Visual; Boulder, CO). For the U87MG tumor burden, tumor volume (mL) was assessed using T1 Gd-DTPA enhanced sequences of the demarcated tumor. For the 0709 primary tumor, tumor burden was assessed using T2 weighted sequences. Given the diffuse nature of the 0709 tumor, tumor burden was calculated on the whole brain volume (mL), by outlining the perimeter of mouse brain.

Statistics

Data are expressed as means t standard error, and comparisons between groups were conducted by a two-tailed unpaired t-test. The survival data was generated using Kaplan-Meier survival plot and groups were compared using the Mantel-Cox test (GraphPad Software, Inc., La Jolla, CA).

Results

Figure 1C:
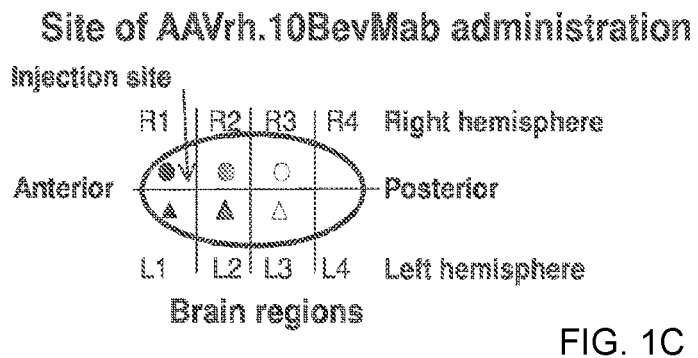
FIGS. 1C-D. AAVrh.10BevMab-mediated expression and function in the mouse CNS. AAVrh.1BevMab ($8 \times 10^{10}$ gc) was administered to the left and right striatum of C57Bl/6 mice. After 4 weeks, the brain was cut into 8 pieces, homogenized and bevacizumab assessed. C) Sites of administration. D) Western analysis using goat anti-human immunoglobulin [light kappa and heavy (IgG)]. Lane 1, PBS; lanes 2-7, AAVrh.10BevMab; lanes 2-4, mouse 1, sites 1-6; lanes 5-7, mouse 2, same sites; lane 8, bevacizumab positive control FIGS. 2A-2H. AAVrh.10BevMab-mediated expression of bevacizumab in neurons of the mouse striatum. Shown is immunofluorescent assessment of coronal sections of the CNS 4 weeks after administration of the PBS control (left panels) or AAVrh.10BevMab (right panels). Neurons were assessed with neuronal nuclear antigen (NeuN) and glia were assessed with anti-glial fibrillary acidic protein (anti-GFAP). A, B) PBS control, anti-human IgG (red). C) PBS control, anti-human IgG (green), NeuN (neurons, red). D) PBS control, anti-human IgG (green), GFAP (red). E, F) AAVrh.10BevMab, anti-human IgG (red). G) AAVrh.10BevMab, anti-human IgG (green), NeuN (neurons, red). H) AAVrh.10BevMab, anti-human IgG (green), GFAP (glia, red). All panels, nuclei counter-stained with DAPI (blue). Panels A, E, bar=100 μm; all other panels, bar=25 μm.
Figure 1D:
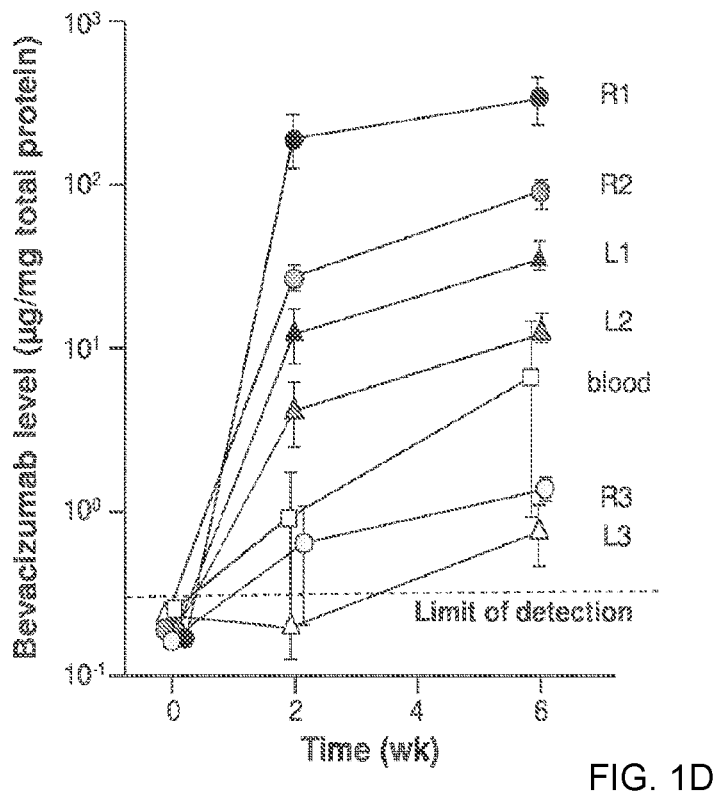

The area of AAVrh.10BevMab administration was compared to other regions of the CNS to assess bevacizumab diffusion in and around the targeted region and absence in non-targeted left hemisphere and posterior regions of the CNS (FIG. 1C). Regional sectioning of the mouse brain followed by ELISA and analysis of total protein showed localized expression of the bevacizumab monoclonal antibody in the area of the administration (FIG. 1D). The targeted area or the right striatum showed the highest expression at 2 weeks, with increased levels at 6 weeks. There was minimal expression in posterior regions and opposite (left) hemisphere of the mouse brain. Importantly, there was minimal bevacizumab (50-fold less as compared to area of AAVrh.10BevMab administration) detected in blood.

Immunohistochemical assessment of the CNS demonstrated AAVrh.10BevMab-directed expression of bevacizumab secreted from neurons in the area of administration (FIG. 2). Control tissue did not show expression (FIGS. 2A-D) while AAVrh.10BevMab treated brains showed expression in the local area of administration (FIGS. 2E-H). Counter-staining of glial cells demonstrated that bevacizumab was not expressed from glia, demonstrating AAVrh.10 specificity for neurons (FIGS. 2G,H).

Figure 3:
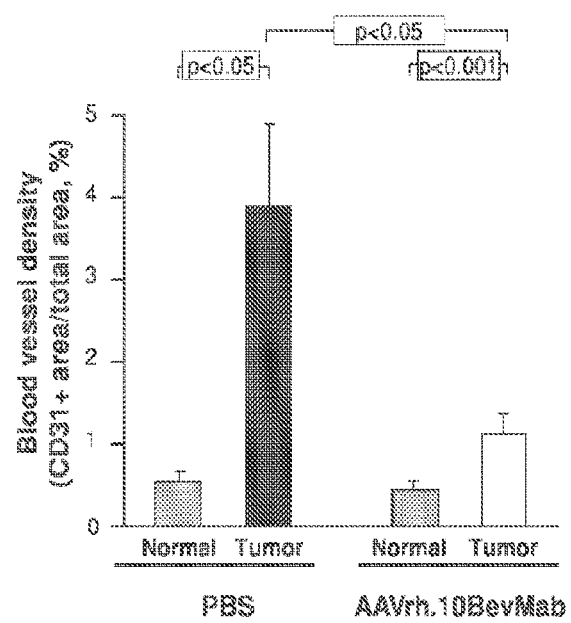
FIG. 3. Quantification of blood vessel density in normal and U87MG tumor tissue of PBS versus AAVrh.10BevMab-treated mice. The U87MG cell line (10 cells) was administered to the right striatum of NOD/SCID immunodeficient mice (n=4 group) at the same time as AAVrh.10BevMab ($5 \times 10^{10}$ gc) or PBS. Quantification of GBM tumor angiogenesis was assessed as blood vessel density/area at 28 days using $CD31^+$ endothelial cell quantification.

AAVrh.10BevMab vector administered concurrently with the U87MG xenograft was assessed for angiogenesis, tumor volume and survival in the mouse brain of NOD/SCID mice. The expression of endothelial cell marker, CD31, was assessed in the tumors and normal tissue. Staining with anti-CD31 showed recruitment of endothelial cells in the area of the GBM tumor of control-treated mice compared to reduced endothelial cell recruitment in AAVrh.10BevMab treated mice. Quantification of tumor blood vessel density showed significant reduction in treated mice (p<0.05; FIG. 3).

Figures 4A, 4B, 4C, 4D:
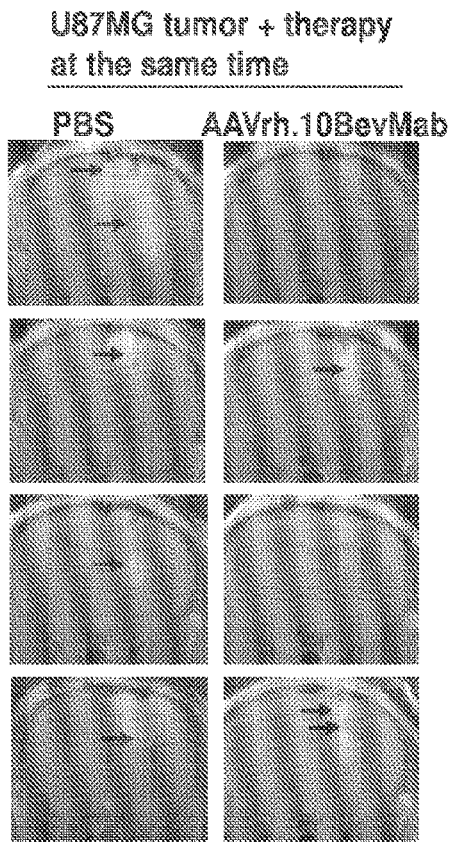
FIGS. 4A-4D. MRI Assessment of tumor volume of mice with U87MG glioblastoma treated with AAVrh.10BevMab or control. U87MG ($10^5$ cells) and AAVrh.10BevMab was administered simultaneously ($5 \times 10^{10}$ gc) (A,B) or 6 days after ($10^{11}$ gc) xenograft (C,D). In A) and C), arrows indicate site of tumor on representative coronal image of striatum. The scans were done at 18 days after U87MG administration. A) MRI, PBS-treated control mice (n=4) and AAVrh.10BevMab-treated mice (n=4). B) Quantification of tumor volumes, PBS-treated (control) versus AAVrh.10BevMab-treated. C) MRI, PBS-control mice (n=6) and AAVrh.10BevMab-treated mice. D) Quantification of tumor volumes at 20 days.
Figure 5A:
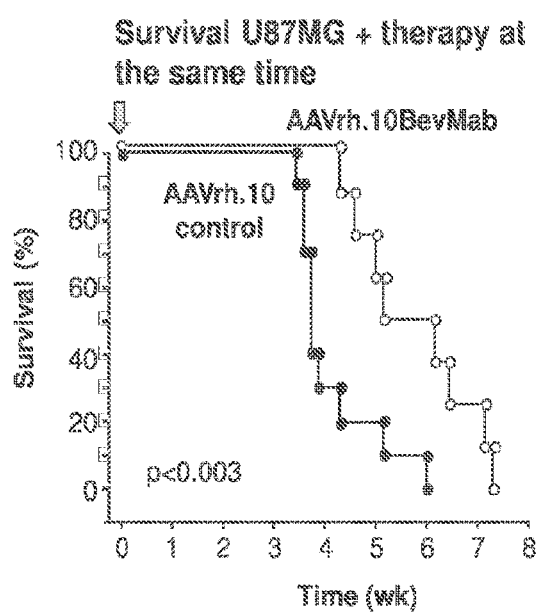
FIGS. 5A-5B. Survival of mice with U87MG human glioblastoma xenografts treated with AAVrh.10BevMab. A) Survival of mice treated simultaneously with AAVrh.10 control or AAVrh.10BevMab (average 33 days or 47 days, respectively); a 31% increase. B) Survival of mice with U87MG human glioblastoma xenografts treated post-xenograft with AAVrh.10control or AAVrh.10BevMab (average 33 days or 54 days, respectively); a 38% increase. Arrow indicates time of treatment.
Figure 5B:
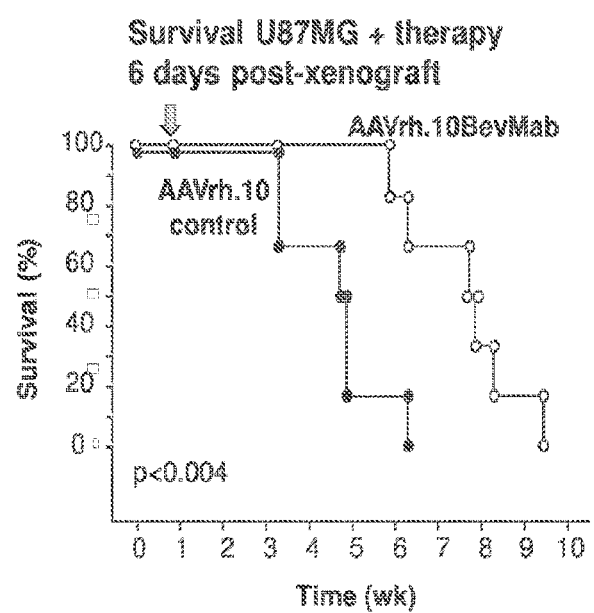

Enhanced MRI imaging of the brains of AAVrh.10BevMab-treated and control-treated mice was used to quantify U87MG tumor growth. Concurrent administration of the U87MG tumor and AAVrh.1BevMab reduced tumor growth by greater than 5-fold at 18 days (p<0.02; FIG. 4A example, panel B—quantification). Likewise, administration of AAVrh.10BevMab to the CNS one week after U87MG GBM xenograft reduced the growth (as measured by MRI) of the U87MG tumor by 2.4-fold at 20 days (p<0.04; FIG. 4C—example; panel B—quantification). Concurrent treatment with AAVrh.10BevMab increased the median survival time of mice with GBM xenografts by 42% (p<0.003; FIG. 5A). Assessment of impact of post-xenograft treatment with AAVrh.10BevMab showed a 64% increase in survival (AAVrh.10BevMab treated vs AAVcontrol, p<0.004; FIG. 5B).

Figure 6A:
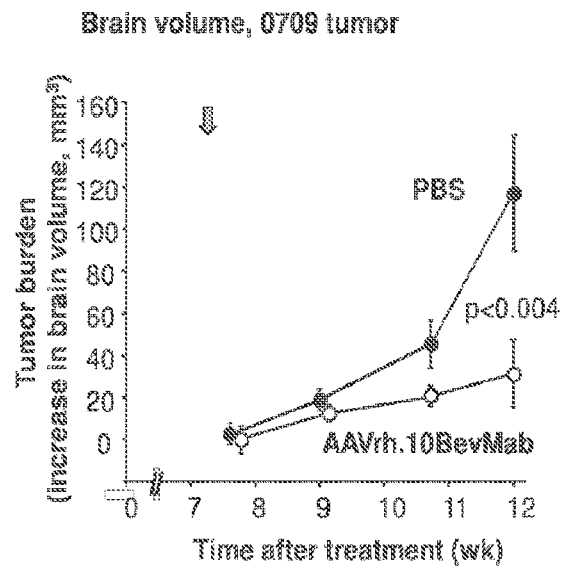
FIGS. 6A-6B. Assessment of tumor burden and survival of mice with low-passage 0709 primary human glioblastoma following treatment with AAVrh.10BevMab. $10^5$ 0709 primary human glioblastoma cells and $10^{11}$ gc were administered to the right hemisphere of NOD/SCID mice (n=20/group). A) MRI quantification of tumor burden over time for PBS control versus AAVrh.10BevMab-treated mice. B) Survival of mice with xenografts treated simultaneously with AAVrh.10BevMab (90%) or AAVrh.10control (52%). For A) and B), arrow indicates time of treatment.
Figure 6B:
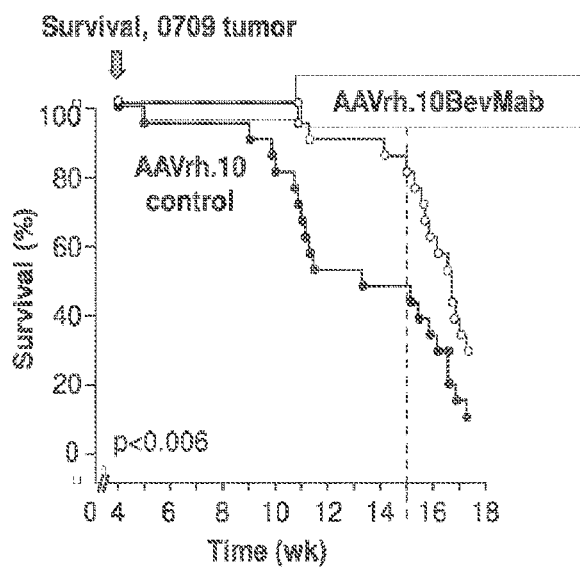

Studies of AAVrh.10BevMab concurrently administered with the 0709 patient-derived early passage GBM primary cells showed a reduction (treated versus control-treated, p<x) in blood vessel density as determined by CD31 and/or lectin staining. There was a reduction in primary tumor burden by 3.3-fold at 12 weeks (treated vs control-treated, p<0.04; FIG. 6A). The primary GBM tumor treated with AAVrh.10BevMab showed a significantly improved survival at 15 weeks (p<0.006: FIG. 6A).

Discussion

A major challenge to developing an effective therapy directed toward glioblastoma is the blood-brain barrier which restricts systemically administered large molecule therapies from reaching the targeted area in the brain. By direct administration of the AAVrh.10BevMab vector to the CNS of immunodeficient mice with human GBM, the blood-brain barrier was bypassed to deliver to neurons the genetic code for the monoclonal antibody bevacizumab. The data demonstrates persistent expression of bevacizumab in the local milieu of the GBM tumor, AAVrh.10BevMab-directed therapy reduced tumor blood vessel density in the area of tumor, a significant reduction in tumor growth and a significant increase in survival in both concurrent and post-xenograft models. AAV-mediated gene transfer of therapeutic monoclonal antibodies directly to the CNS overcomes a common hurdle to anti-tumor therapy, the blood-brain barrier, and through local and persistent expression, provides therapy for human GBM.

REFERENCES

Aahdini et al., *World Neurosurg.*, 73:128 (2010).
Altaner, *Neoplasma.*, 55:369 (2008).
Anonymous, *Nature*, 455:1061 (2008).
Barbero et al., *Cancer Res.*, 63:1969 (2003).
Barker et al., *Neurosurgery*, 42:709 (1998).
Batra et al., *Hybridoma*, 13:87 (1994).
Beers et al., *Clin. Cancer Res.*, 6:2835 (2000).
Berdoz et al., *PCR Methods Appl.*, 4:256 (1995).
Bertulini et al., *Cancer Res.*, 62:3106 (2002).
Bird et al., *Science*, 242:423426 (1988).
Blanchetor et al., *J. Biol. Chem.*, 288:25173 (2013).

Boockvar et al., *J. Neurosurg.*, 114:624 (2010).
Bouliane et al., *Nature*, 12:643 (1984).
Brennan et al., *PLoS One.*, 4:e7752 (2009).
Brigham et al., *J. Liposome Res.*, 3:31 (1993).
Carrera et al., *Proc. Natl. Acad. Sci. U.S.A.*, 97:6202 (2000).
Carson et al., *Adv. Immunol.*, 38:274 (1986).
Chiang et al., *Biotechniques*, 7:360 (1989).
Chonn et al., *Curr. Opin. Biotech.*, 6:698 (1995).
Christensen et al., *J. Neurooncol.*, 104:129 (2011).
Cole et al., *Mol. Cell. Biochem.*, 62:109 (1984).
Deorah et al., *Neurosurg. Focus*, 20:E1 (2006).
di et al., *Cancer Res.*, 71:19 (2011).
do et al., *Cancer Biol. Ther.*, 9:56 (2010).
Ehtesham et al., *Cancer Lett.*, 274:305 (2009).
Ehtesham et al., *Oncogene*, 25:2801 (2006).
Ferrara, *Arterioscler. Thromb. Vasc. Biol.*, 259:789 (2009).
Galfrascoli et al., *Dig. Liver Dis.*, 43:286 (2010).
Gan et al., *J. Clin. Neurosci.*, 16:748 (2009).
Gavilondo & Larrick, *Biotechniques*, 22:128 (2000).
Gilbertson and Rich, *Nat. Rev. Cancer.*, 7:733 (2007).
Gupta et al., *BMC Biotechnol.*, 10:72 (2010).
Harvey et al., *Hum. Gene Ther.*, 13:15 (2002).
Harvey et al., *J. Virol.*, 7:6729 (1999).
Hess et al., *Cancer*, 101:2293 (2004).
Hoang et al., *Clin. Orthop. Relat. Res.*, 426:32 (2004).
Homsi and Daud, *Cancer Control.* 14:285 (2007).
Hovinga et al., *Stem Cells*, 28:1019 (2010).
Huang et al., *Sci. Signal.* 2:re6 (2009).
Hunkapiller and Hood, *Nature*, 323:15 (1986)
Huston et al., *Proc. Natl. Acad. Sci. U.S.A.*, 85:5879 (1988)
Huston & George, *Hum. Antibodies*, 10:127 (2001).
Jalanko and Braulke, *Biochim Biophys Acta*, 1793:697 (2009).
Jenab-Wolcott and Giantonio, *Expert Opin. Biol. Ther.*, 9:507 (2009).
Jones et al., *Nature*, 321:522 (1986).
Junck, *Neurology*, 76:414 (2011).
Kipriyanov & Le Gall, *Mol. Biotechnol.*, 2:39 (2004).
Knizetova et al., *Cell Cycle*, 7:2553 (2008).
Kohler and Milstein, *Nature*, 2:495 (1975).
Kourlas and Abrams, *Clin. Ther.*, 29:1850 (2007).
Koutcher et al., *Clin. Cancer Res.*, 6:1498 (2000).
Kozbor et al., *Immunol. Today*, 4:72 (1983).
Kuhne et al., *Clin. Cancer Res.*, 19:357 (2013).
Langer and Soria, *Clin. Luna Cancer*, 11:82 (2010).
Lanzavecchia et al., *Eur. J. Immunol.*, 17:105 (1987).
Larrick et al., *Biochem Biophys. Res. Commun.*, 160:1250 (1989).
Ledley, *Human Gene Therapy.*, 6:1129 (1995).
Lee et al., *PLoS Med.*, 3:e485 (2006).
Lonberg & Huszar, *Int. Rev. Immunol.*, 13:65 (1995).
Lopez-Gines et al., *Mod, Pathol.*, 23:856 (2010).
Lottaz et al., *Cancer Res.*, 70:2030 (2010).
Lu et al., *Cancer Chemother. Pharmacol.*, 62:779 (2008).
Miller et al., *FASEB Journal*, 9:190 (1995).
Morrison et al., *Proc. Nat. Acad. Sci. U.S.A.*, 86:6851 (1984).
Morrison et al., *Proc. Natl. Acad. Sci. U.S.A.*, 81:6851 (1984).
Morrison, *Annu. Rev. Immunol.*, 12:239 (1992).
Murakami et al., *J. Virol.*, 73:7489 (1999).
Ohgaki and Kleihues, *Am. J. Pathol.*, 170:1445 (2007).
Orlandi et al., *Proc. Natl. Acad. Sci. U.S.A.*, 86:3833 (1989).
Park et al., *J. Clin. Oncol.*, 28:3838 (2010).
Peak and Levin, *Cancer Manag. Res.*, 2:97 (2010).
Piccirillo et al., *J. Mol. Med.*, 87:1087 (2009).
Pogue et al., Patent application number: 20100158902 (2011).
Pope et al., *Neurology*, 76:432 (2011).
Sandhu, *Crit. Rev. Biotechnol.*, 12:437 (1992).
Schofield et al., *British Med. Bull.*, 51:56 (1995).
Schwartz et al., *Proc. Am. Soc. Clin. Oncol.*, 21:24 (2002).
Shinojima et al., *Cancer Res.*, 63:6962 (2003).
Sofer-Podesta et al., *Infect. Immun.*, 77:1561 (2009).
Sondhi et al., *Gene Ther.*, 12:1618 (2005).
Sondhi et al., *Mol. Ther.*, 15:481 (2007).
Souweidane et al., *J. Neurosurg. Pediatr.*, 6:115 (2010).
Stevenson et al., *Neurosurgery.*, 63:560 (2008).
Thompson et al., *Neurology.*, 76:87 (2011).
Vaday et al., *Clin. Cancer Res*, 12:5630 (2004).
Van Meir et al., *CA Cancer J. Clin.*, 60:166 (2010).
Verhaak et al., *Cancer Cell*, 17:98 (2010).
Verhoeven et al., *Science*, 239:1534 (1988).
Wang et al., *Cancer Gene Ther.*, 17:559 (2010).
Wang et al., *Nature*, 468:829 (2010).
Watanabe et al., *Hum. Gene Ther.*, 19:300 (2008).
Worgall et al., *Hum. Gene Ther.*, 19:463 (2008).
Wu et al., *J. Cell Biochem.*, 103:245 (2008).
Zagzag et al., *Lab Invest.*, 86:1221 (2006).
Zhong et al., *Clin. Cancer Res.*, 19:4433 (2013).

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed:

1. A method of inhibiting glioblastoma, a glioma or a glial tumor in a human, comprising: intracranially or intracisternally administering to the human, during or after resection of the glioblastoma, glioma or glial tumor, a composition comprising an effective amount of a recombinant adeno-associated virus (rAAV) comprising:
   i) an expression vector encoding an antibody directed against vascular endothelial growth factor (VEGF), wherein the antibody comprises SEQ ID NO:4 and SEQ ID NO:5; or ii) an expression vector encoding an antibody directed against epidermal growth factor receptor (EGFR), wherein the antibody comprises SEQ ID NO:8 and SEQ ID NO:9, wherein the rAAV comprises an AAVrh10 capsid.

2. The method of claim 1 wherein the amount is effective to reduce tumor volume or blood vessel density.

3. The method of claim 1 wherein the antibody that is expressed in the central nervous system of the mammal comprises two heavy chains and two light chains.

4. The method of claim 1 wherein the human has glioblastoma, a glial tumor, an astrocytoma, grade 1 glioma, grade 2 glioma, an oligodendroglioma, a neurocytoma, a dysplastic neuroepithelial tumor, a primitive neuroectodermal tumor, or a ganglioneuroma.

5. The method of claim 1 wherein the antibody is a chimeric or humanized antibody.

6. The method of claim 1 wherein the expression vector encodes the anti-VEGF antibody.

7. The method of claim 1 wherein the expression vector encodes the anti-EGFR antibody.

8. The method of claim 7 wherein the antibody binds to EGFRVIII.

9. The method of claim 1 wherein the composition does not include a permeation enhancing agent.

10. The method of claim 1 wherein the administration occurs during cancer resection.

11. The method of claim 1 wherein the human has glioblastoma.

12. The method of claim 1 wherein the administration is via a cannula or needle.

13. The method of claim 1 wherein the human has glioblastoma and the rAAV is intracranially administered.

14. The method of claim 1 wherein the human has glioblastoma and the rAAV is intracisternally administered.

* * * * *

SEQUENCE LISTING

```
<160> NUMBER OF SEQ ID NOS: 15

<210> SEQ ID NO 1
<211> LENGTH: 188
<212> TYPE: PRT
<213> ORGANISM: Homo sapien

<400> SEQUENCE: 1

Met Asn Leu Val Val Tyr Leu Ile Gln Leu Phe Leu Ala Ala Leu Leu
1               5                   10                  15

His Leu Ser Ala Val Lys Ala Ala His Ile Pro Lys Glu Gly Gly Lys
            20                  25                  30
```

-continued

```
Ser Lys Asn Asp Val Ile Pro Phe Met Asp Val Tyr Lys Ser Ala
        35                  40                  45

Cys Lys Thr Arg Glu Leu Leu Val Asp Ile Ile Gln Glu Tyr Pro Asp
 50                  55                  60

Glu Ile Glu His Thr Tyr Ile Pro Ser Cys Val Val Leu Met Arg Cys
 65                  70                  75                  80

Ala Gly Cys Cys Asn Asp Glu Ala Leu Glu Cys Val Pro Thr Glu Thr
                 85                  90                  95

Arg Asn Val Thr Met Glu Val Leu Arg Val Lys Gln Arg Val Ser Gln
                100                 105                 110

His Asn Phe Gln Leu Ser Phe Thr Glu His Thr Lys Cys Glu Cys Arg
            115                 120                 125

Pro Lys Ala Glu Val Lys Ala Lys Lys Glu Asn His Cys Glu Pro Cys
        130                 135                 140

Ser Glu Arg Arg Lys Arg Leu Tyr Val Gln Asp Pro Leu Thr Cys Lys
145                 150                 155                 160

Cys Ser Cys Lys Phe Thr Gln Met Gln Cys Lys Ser Arg Gln Leu Glu
                165                 170                 175

Leu Asn Glu Arg Thr Cys Arg Cys Glu Lys Pro Arg
            180                 185

<210> SEQ ID NO 2
<211> LENGTH: 1210
<212> TYPE: PRT
<213> ORGANISM: Homo sapien

<400> SEQUENCE: 2

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
                 20                  25                  30

Gly Thr Ser Asn Lys Leu Thr Gln Leu Gly Thr Phe Glu Asp His Phe
             35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
        210                 215                 220
```

```
Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640
```

```
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
        995                 1000                1005
Asp Val Val Asp Ala Asp Glu Tyr Leu Ile Pro Gln Gln Gly Phe Phe
    1010                1015                1020
Ser Ser Pro Ser Thr Ser Arg Thr Pro Leu Leu Ser Ser Leu Ser Ala
1025                1030                1035                1040
Thr Ser Asn Asn Ser Thr Val Ala Cys Ile Asp Arg Asn Gly Leu Gln
                1045                1050                1055
Ser Cys Pro Ile Lys Glu Asp Ser Phe Leu Gln Arg Tyr Ser Ser Asp
```

Pro Thr Gly Ala Leu Thr Glu Asp Ser Ile Asp Asp Thr Phe Leu Pro
                1075                1080                1085

Val Pro Glu Tyr Ile Asn Gln Ser Val Pro Lys Arg Pro Ala Gly Ser
                1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
                1140                1145                1150

Ser Pro Ala His Trp Ala Gln Lys Gly Ser His Gln Ile Ser Leu Asp
                1155                1160                1165

Asn Pro Asp Tyr Gln Gln Asp Phe Phe Pro Lys Glu Ala Lys Pro Asn
                1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210

<210> SEQ ID NO 3
<211> LENGTH: 93
<212> TYPE: PRT
<213> ORGANISM: Homo sapien

<400> SEQUENCE: 3

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 4
<211> LENGTH: 231
<212> TYPE: PRT
<213> ORGANISM: Artificial Sequence
<220> FEATURE:
<223> OTHER INFORMATION: A synthetic amino acid sequence

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
                35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr
225                 230

<210> SEQ ID NO 5
<211> LENGTH: 214
<212> TYPE: PRT
<213> ORGANISM: Artificial Sequence
<220> FEATURE:
<223> OTHER INFORMATION: A synthetic amino acid sequence

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 6
<211> LENGTH: 214
<212> TYPE: PRT
<213> ORGANISM: Artificial Sequence
<220> FEATURE:
<223> OTHER INFORMATION: A synthetic amino acid sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 231
<212> TYPE: PRT
<213> ORGANISM: Artificial Sequence
<220> FEATURE:
<223> OTHER INFORMATION: A synthetic amino acid sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr

```
                65                  70                  75                  80
Leu Gln Met Asn Ser Leu Arg Ala Glu Asp Thr Ala Val Tyr Tyr Cys
                    85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr
225                 230

<210> SEQ ID NO 8
<211> LENGTH: 452
<212> TYPE: PRT
<213> ORGANISM: Artificial Sequence
<220> FEATURE:
<223> OTHER INFORMATION: A synthetic amino acid sequence

<400> SEQUENCE: 8

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
                35                  40                  45

Gly Val Ile Trp Ser Gly Gly Asn Thr Asp Tyr Asn Thr Pro Phe Thr
            50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
```

```
            195                 200                 205
Ser Asn Thr Lys Val Asp Lys Arg Val Glu Pro Lys Ser Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 9
<211> LENGTH: 213
<212> TYPE: PRT
<213> ORGANISM: Artificial Sequence
<220> FEATURE:
<223> OTHER INFORMATION: A synthetic amino acid sequence

<400> SEQUENCE: 9

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
```

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 10
<211> LENGTH: 452
<212> TYPE: PRT
<213> ORGANISM: Artificial Sequence
<220> FEATURE:
<223> OTHER INFORMATION: A synthetic amino acid sequence

<400> SEQUENCE: 10

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
```

```
                    245                 250                 255
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 11
<211> LENGTH: 213
<212> TYPE: PRT
<213> ORGANISM: Artificial Sequence
<220> FEATURE:
<223> OTHER INFORMATION: A synthetic amino acid sequence

<400> SEQUENCE: 11

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
        Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Ala
                        210

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15
<211> LENGTH: 258
<212> TYPE: PRT
<213> ORGANISM: Artificial Sequence
<220> FEATURE:
<223> OTHER INFORMATION: A synthetic amino acid sequence

<400> SEQUENCE: 15

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
                35                  40                  45

Tyr Glu Met Glu Glu Asp Gly Val Arg Lys Cys Lys Lys Cys Glu Gly
        50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
                100                 105                 110

Ser Phe Thr His Thr Pro Pro Leu Asp Pro Gln Glu Leu Asp Ile Leu
                115                 120                 125

Lys Thr Val Lys Glu Ile Thr Gly Phe Leu Leu Ile Gln Ala Trp Pro
            130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
```

-continued

```
                180                 185                 190
Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
        210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser
```